(12) United States Patent
Auld

(10) Patent No.: US 7,812,318 B1
(45) Date of Patent: Oct. 12, 2010

(54) ELECTROMAGNETIC BIOSENSOR

(75) Inventor: Jeffrey R. X. Auld, Raleigh, NC (US)

(73) Assignee: Advanced Technology Applications, LLC, Morgantown, WV (US)

(*) Notice: Subject to any disclaimer, the term of this patent is extended or adjusted under 35 U.S.C. 154(b) by 30 days.

(21) Appl. No.: 12/049,012

(22) Filed: Mar. 14, 2008

(51) Int. Cl.
*G01T 1/00* (2006.01)
*G01N 33/53* (2006.01)

(52) U.S. Cl. ........................ 250/395; 435/7.1

(58) Field of Classification Search ............... 250/395, 250/458.1; 435/6, 7.1, 287.2; 436/43, 45
See application file for complete search history.

(56) References Cited

U.S. PATENT DOCUMENTS

| | | | |
|---|---|---|---|
| 5,377,003 | A | 12/1994 | Lewis et al. |
| 5,732,150 | A | 3/1998 | Zhou et al. |
| 5,784,162 | A | 7/1998 | Cabib et al. |
| 6,110,748 | A | 8/2000 | Reber et al. |
| 6,153,743 | A | 11/2000 | Hubbell et al. |
| 6,632,399 | B1 | 10/2003 | Kellogg et al. |
| 6,660,147 | B1 | 12/2003 | Woudenberg et al. |
| 6,719,682 | B2 | 4/2004 | Kellogg et al. |
| 6,727,103 | B1 | 4/2004 | Reber et al. |
| 6,734,401 | B2 | 5/2004 | Bedingham et al. |
| 6,749,736 | B1 | 6/2004 | Fuhr et al. |
| 6,770,441 | B2 | 8/2004 | Dickinson et al. |
| 6,818,435 | B2 | 11/2004 | Carvalho et al. |
| 6,878,555 | B2 | 4/2005 | Andersson et al. |
| 6,884,395 | B2 | 4/2005 | Tooke et al. |
| 6,887,701 | B2 | 5/2005 | Anderson et al. |
| 6,913,931 | B2 | 7/2005 | Halverson et al. |
| 6,916,372 | B2 | 7/2005 | David |
| 6,919,058 | B2 | 7/2005 | Andersson et al. |
| 6,937,323 | B2 | 8/2005 | Worthington et al. |
| 6,942,804 | B2 | 9/2005 | Herman |
| 7,200,088 | B2* | 4/2007 | Worthington et al. ..... 369/53.31 |
| 2002/0137218 | A1* | 9/2002 | Mian et al. ................. 436/45 |
| 2003/0215825 | A1* | 11/2003 | Tong ............................ 435/6 |
| 2005/0037484 | A1* | 2/2005 | Staimer et al. ........... 435/287.2 |

OTHER PUBLICATIONS

Hardiman, Gary, Microarray platforms—comparisons and contrasts, Pharmacogenomics, 2004, pp. 487-502, Future Medicine Ltd., ISSN: 1462-2416.
Data interchange on read-only 120 mm optical data disks (CD-ROM), Standard ECMA—130, 2nd Edition, Jun. 1996.
120 mm DVD Rewritable Disk (DVD-RAM), Standard ECMA—272, 2nd Edition, Jun. 1999.
120 mm DVD—Read-Only Disk, Standard ECMA—267, 3rd Edition, Apr. 2001.

* cited by examiner

*Primary Examiner*—David P Porta
*Assistant Examiner*—Faye Boosalis
(74) *Attorney, Agent, or Firm*—Thompson Hine LLP

(57) ABSTRACT

A system, method, device, and process for making and using an electromagnetic-sensitive biosensor on a biosensor disk to identify and classify an analyte in a sample. The biosensor of the biosensor disk is exposed to a sample containing analytes and a desired analyte adheres to the biosensor. The biosensor disk is rotated during operation and an electromagnetic emitter directs an electromagnetic radiation beam at the biosensor disk. The returned electromagnetic radiation from the biosensor disk is received by a sensor that converts the returned electromagnetic radiation into a signal to indicate the presence of the desired analyte in the sample.

25 Claims, 11 Drawing Sheets

100

120

200

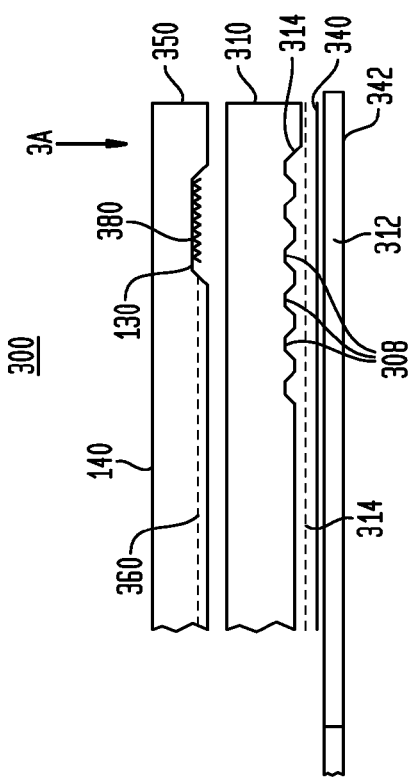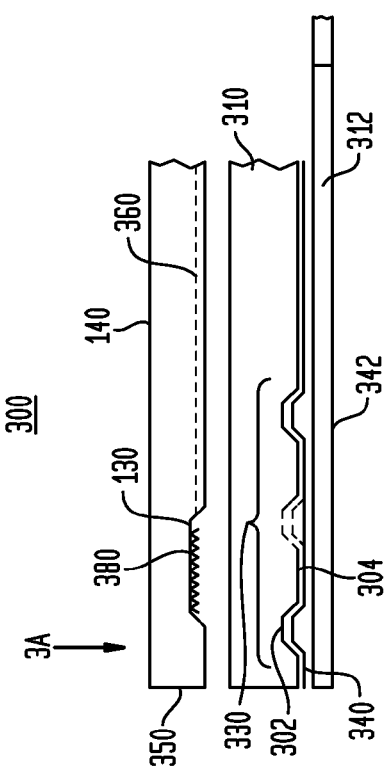

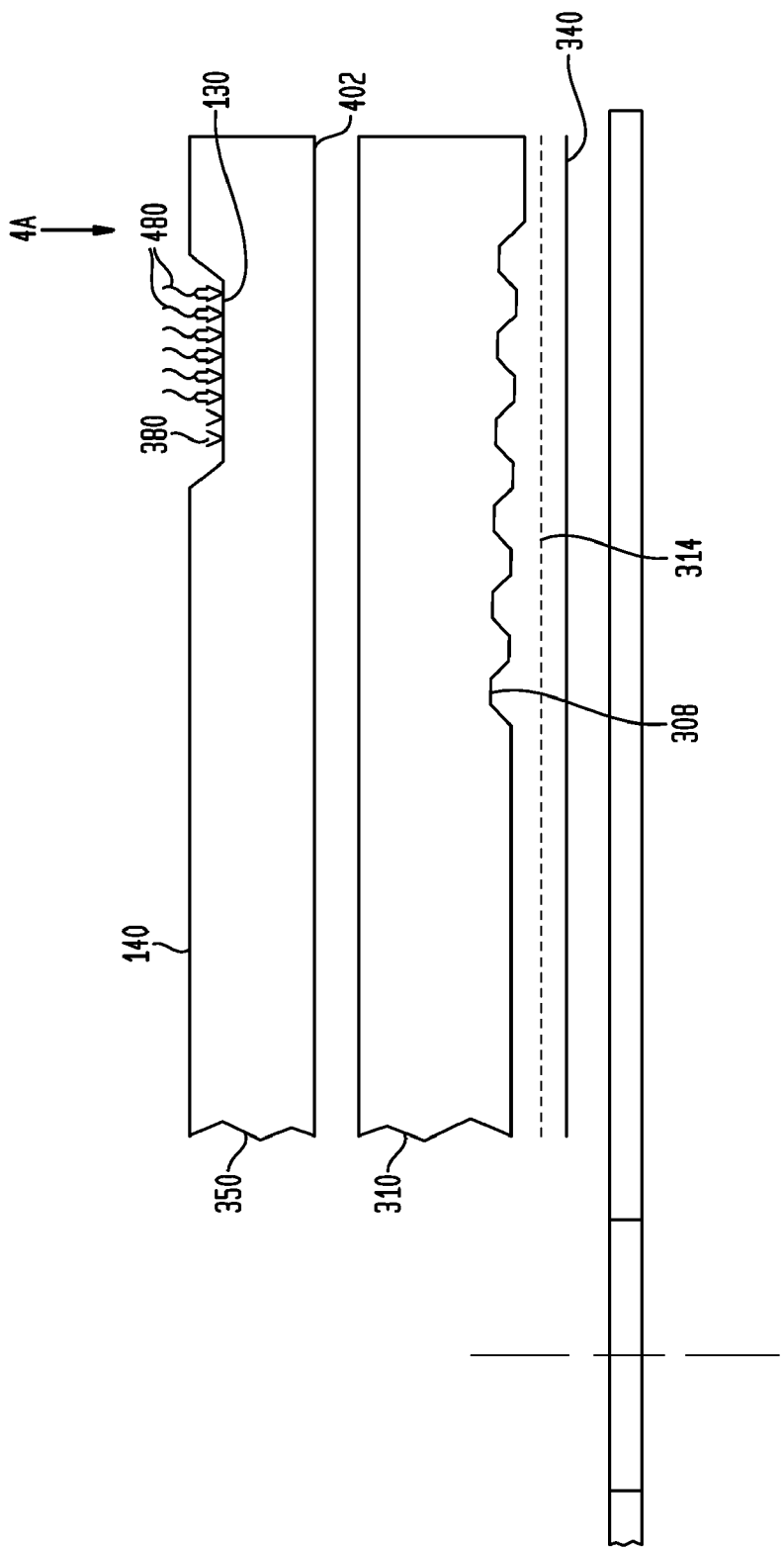

ELECTROMAGNETIC BIOSENSOR

TECHNICAL FIELD

The present invention relates to devices, methods, and processes for using biologically active compounds and electromagnetic sensors to detect and classify analytes.

BACKGROUND

Biosensor systems are analytic devices that are capable of detecting and, in many cases, estimating the relative concentration of specific substances, commonly called analytes, and other parameters of biological interest. The analytes detected can be both inorganic or organic in nature. Biosensor systems provide a response that is modulated by the presence of one or more specific analytes in order to provide information to a user that an analyte is present in the system and possibly an estimate of the concentration of the analyte.

Analytes, when present, are often in very low concentrations, are often sub-millimeter or smaller in size, and are therefore difficult to detect without sensitive equipment designed specifically to detect their presence. Often, the substance to be analyzed is exposed to additional chemicals that attach to the analytes to tag or mark them. With the addition of the chemical markers, the tagged analytes become much bigger, respond differently to specific frequencies of incident light, crystallize, or otherwise change physical properties in some way that makes them easier to detect. Existing biosensor systems can be expensive to own and often require advanced technical expertise to operate safely and effectively. Subsequently, most individuals do not have access to, or sufficient knowledge of, the sophisticated laboratory equipment necessary to detect most analytes.

Therefore, when there is a need to have a substance analyzed, lab personnel or a specialist from, for example, the local forensics department, will collect a sample and take it back to a laboratory for analysis. This entails at least three problems. First there is a time lag between when the sample is sent to the laboratory and when results are available. Second, there is a sample durability issue wherein the analyte may change chemically during the time lag between when the sample is taken and when it is analyzed. And third, there is the cost of transporting the sample and having it analyzed by a laboratory. It would often be advantageous to equip individuals with the ability to detect certain analytes in situ in real time.

Rotating electromagnetic disks, including optical disks commonly used for transferring digital information such as compact disks (CDs) and Digital Video Disks (DVDs), use electromagnetic radiation to read digital information encoded on the surface of the disk. These rotating optical disks provide a convenient means for storing digital information in a portable device. Electromagnetic sensor disks store information using structures that are on the order of a micrometer in scale and packed closely together on the order of a few micrometers. Devices for reading and interpreting the information stored on rotating electromagnetic disks are very common, with many persons having ready access to a number of different devices for reading the information. These common devices can resolve the micrometer structures for storing date and can therefore can also be used resolve tagged analytes of similar scale.

There is a need for a method, device, and process for creating, reading, and evaluating analytes using an electromagnetic sensor disk. The additional ability to use some embodiments of the electromagnetic sensor disk with existing electronic devices, including consumer electronics, audio players, and computers for reading the sensed analyte information provides additional flexibility and utility.

BRIEF DESCRIPTION OF THE DRAWINGS

The accompanying figures depict multiple embodiments of the device, method, and processes for using an electromagnetic biosensor to determine and classify analytes. A brief description of each figure is provided below. Elements with the same reference numbers in each figure indicate identical or functionally similar elements. Additionally, the left-most digit(s) of a reference number identifies the drawings in which the reference number first appears.

FIG. 3a is a cross-sectional view of a biosensor disk of a first embodiment, wherein said detection chambers are constructed in a sandwich on the surface of an electromagnetic disk with permanently encoded data.

FIG. 3b is a cross-sectional view of a biosensor disk of a another embodiment, wherein said detection chambers are constructed in a sandwich on the surface of an electromagnetic disk with the ability to record data.

FIG. 4 is a cross-sectional view of a biosensor disk of a second embodiment, wherein said detection chambers are constructed on the exposed surface of an electromagnetic disk.

DETAILED DESCRIPTION

Structure of a Biosensor Disk

Figure 1A:
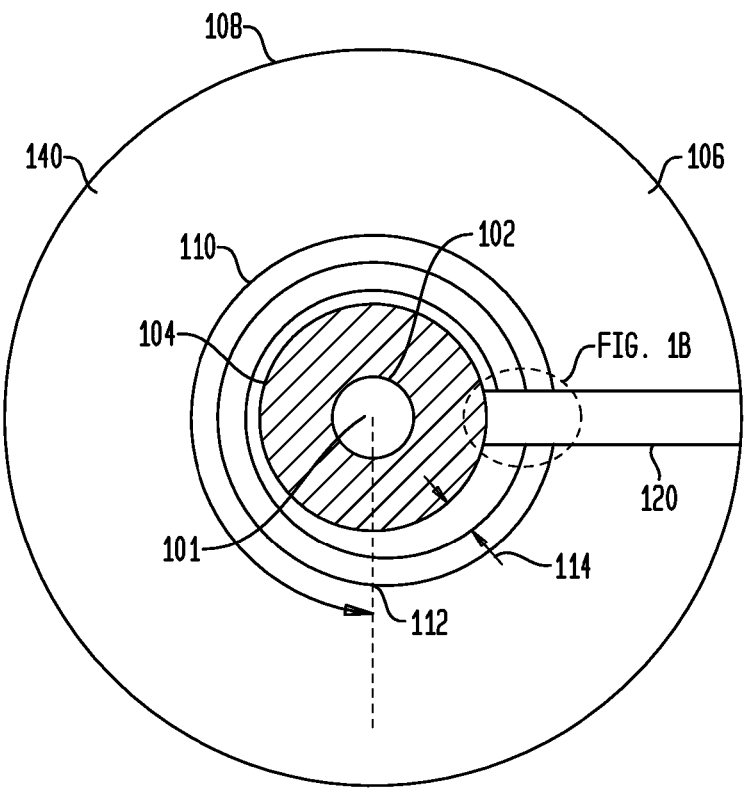
FIG. 1A is a view of the top surface of a biosensor disk with a depiction of a continuous spiral data track and an area of detector chambers.

FIG. 1 depicts the top surface 140 of a biosensor disk 100. The biosensor disk 100 in this embodiment is configured with approximately the same dimensions as a compact disc (CD).

The biosensor disk 100 can be configured to a number of different sizes, shapes, and configurations, and in this embodiment, the size of a standard audio CD was selected for convenience only. The biosensor disk 100 has a center 101 and a center hole 102 aligned with the center 101. The center hole 102 is formed through the main body of the biosensor disk 100 and is roughly cylindrical in shape through the center 101 of the biosensor disk 100. In the case of a biosensor disk 100 adapted to conform with CD standards, the center hole 102 is approximately 15 mm in diameter. Moving outward from the center hole 102 on the surface of the biosensor disk 100 is the transition area 104. The transition area 104 has a diameter of about 44 mm. The outer surface area of the biosensor disk 100 between the transition area 104 to the outer edge 108 is the information area 106.

The information area 106 of the biosensor disk 100 has a continuous data spiral 110. The continuous data spiral 110 extends from the edge of the transition area 104 and spirals outward toward the outer edge 108. A single physical track 112 is defined as one complete turn, 360 degrees, of the continuous data spiral 110 on any arbitrary portion of the data spiral 110. The track to track separation 114 of a standard CD is 1 μm, while a DVD is measured as 0.7 μm. The track-to-track separation 114 of the biosensor disk 100 embodiment shown in FIG. 1A is about 1.6 μm. Other embodiments of the biosensor disk 100 have larger or smaller track-to-track separation 114 based on a number of factors including the type of device used to read the biosensor disk 100, the type of analyte being detected, and the method of creating the detector ligands 380 as described herein.

The biosensor disk 100 of the embodiment shown in FIG. 1A has a discrete analyte detector region 120. The analyte detector region 120 extends roughly from the inner diameter of the information area 106 to the outer edge 108, covering approximately the same radial position on the surface of the biosensor disk 100. In one embodiment, the detector region 120 is roughly rectangular in shape with parallel sides. In an alternate embodiment, the detector region 120 is more of a pie shape and has sides that diverge the further they are displaced from the center 101, for example the sides can be portions of a radius of the biosensor disk 100.

Figure 1B:
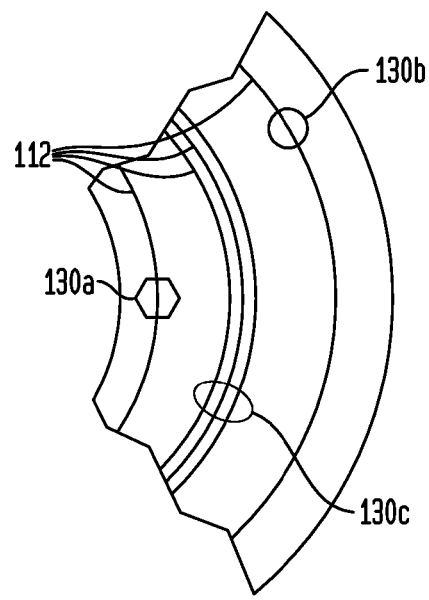
FIG. 1B is a close-up view of the top surface of a biosensor disk highlight specific features found in the area of the detector chambers.

A small portion of the analyte detector region 120 is shown in detail in FIG. 1B. The analyte detector region 120 is comprised of multiple types of detector chambers 130a, 130b, 130c, and collectively 130. The detector chambers 130 are displaced on the biosensor disk 100 relative to the continuous data spiral 110 and specifically the individual physical tracks 112. The detector chambers 130 are configured such that they overlap either partially or completely the track of at least one physical track 112, as in the case of the hexagonal detector chamber 130a and the circular detector chamber 130b. Other detector chambers 130 are configured to substantially overlap more than one physical tracks 112. In some embodiments, described in detail later, the detector chambers 130 are at the same depth in the biosensor disk 100 as the physical track 112. In other embodiments, the detector chambers 130 are located between the physical track 112 and the top surface 140 of the biosensor disk 100. In still other embodiments, the detector chambers 130 are located on the top surface 140 of the biosensor disk 100 or on a separate element that is integrated onto the biosensor disk 100.

In an alternate embodiment, the detector chambers 130 are replaced with one or more binding sites that reside on the analyte detector region 120. In an alternate embodiment, the analyte detector region 120 is pressed into a corresponding groove in the biosensor disk 100.

Disk System

Figure 2:
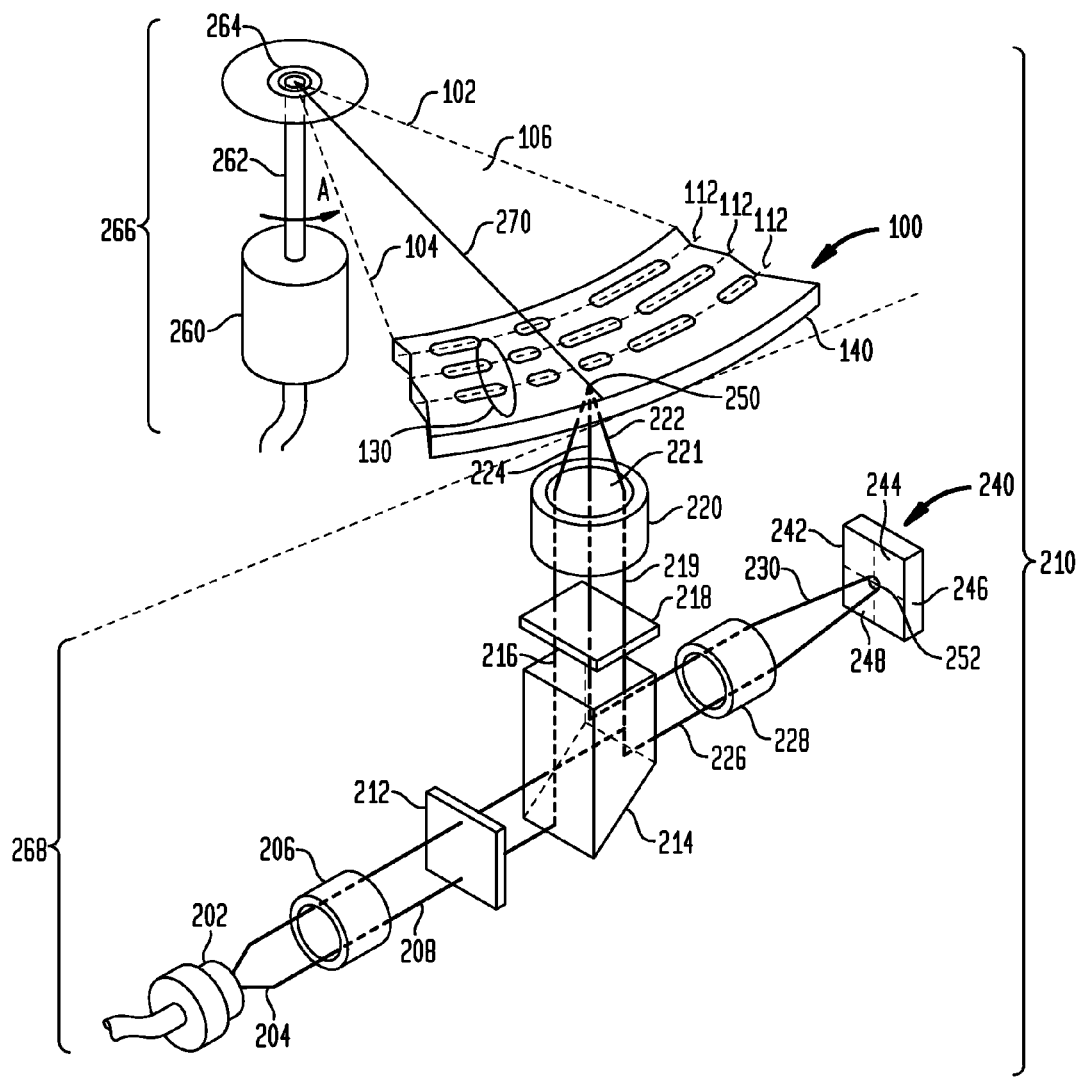
FIG. 2 is a view of a disk system that uses electromagnetic radiation to read information encoded on a biosensor disk in the continuous spiral data track including an area with a detector chamber present.

A schematic of one embodiment of a disk read/write system, or more generally a disk system 200 is shown in FIG. 2. The disk system 200 is comprised of a disk rotation system 266, and a radiation emitter and detection system 268. The disk system 200 is integrated together with a biosensor disk 100 to create the biosensor system 210. The disk system 200 is comprised of multiple components to rotate the biosensor disk 100, generate electromagnetic radiation, focus the electromagnetic radiation approximately on the top surface 140 of the biosensor disk 100, receive reflected radiation, and interpret and process the reflected radiation to generate useable signals. The term "reflected radiation", used hereafter for convenience, should be interpreted broadly to comprise the returned radiation resulting from the incidence of electromagnetic radiation on the biosensor disk 100 as would be understood by those of skill in the art. Detectable changes to the returned radiation include, but are not limited to, changes due to absorption, reflection, dispersion, transmission, refraction, and diffraction of the electromagnetic radiation by the biosensor disk 100.

The disk system 200 has a radiation emitter 202 that produces source radiation 204 within a specific wavelength range. The radiation emitter 202 in some embodiments produces source radiation 204 at a relatively constant power or intensity level. In other embodiments, the radiation emitter 202 produces source radiation 204 at two or more power levels. In the case of one embodiment of the disk system 200 adapted for CD media, the radiation emitter 202 is a solid state laser or light emitting diode (LED) generating light between about 760 nm and 790 nm. In the case of an embodiment of the disk system 200 adapted for DVD media, the radiation emitter 202 is a solid state laser or light emitting diode (LED) generating light between about 640 nm to 660 nm or about 400 nm to about 410 nm. Alternative radiation emitters 202 can be used based on the selective physical characteristics of the biosensor disk 100 including reflectivity and the composition of the continuous data spiral 110, the detector chambers 130, detector ligands 380, and other parameters known to those of skill in the art.

The next element of the disk system 200 is the collimator lens 206. The collimator lens 206 is adapted to collimate the incoming source radiation 204, such that the output is collimated radiation 208 with parallel waves and a plane wavefront. In the embodiment shown, the collimator lens 206 is a parabolic concave lens with the radiation source 202 at the focus of the mirror. Other methods of collimating the source radiation 204 into collimated radiation 208 can be used as known to those of ordinary skill in the art.

The embodiment shown in FIG. 2 also includes a diffraction grating 212. The diffraction grating 212 effectively splits the collimated radiation 208 into a single main central peak and two secondary peaks on each side of the main central peak. The diffraction grating 212 is not present in other embodiments of the disk system 200.

The next element in this embodiment of the disk system 200 shown in FIG. 2 is the polarizing prism 214. The polarizing prism 214 polarizes the incoming collimated radiation 208 and emits linearly polarized collimated radiation 216 toward the quarter wave plate 218. The polarizing prism 214 in this embodiment enables the incoming collimated radiation 208 to be emitted toward the biosensor disk 100, while enabling the reflected radiation 224 to be directed toward the radiation detector 240. The separation of the incoming collimated radiation 208 from the reflected radiation 224 is achieved in the polarizing prism 214 of this embodiment of the disk system 200 and is constructed from two prisms of birefringent material, that direct the light unequally in different direction bonded together (bond line not shown) along a diagonal to direct the radiation. The planar physical arrangement of the radiation emitter 202 and the radiation detector 240 is a matter of convenience and is selected in this case due to the ability to create a relatively flat structure and minimize the total depth of the disk system 200. In another embodiment of the disk system 200, the radiation emitter 202 and the radiation detector 240 have separate radiation paths and they are co-located over the surface of the biosensor disk 100. In still another embodiment of the disk system 200, the radiation emitter 202 faces one surface of the biosensor disk 100 while a collecting lens is mounted facing the opposite surface of the biosensor disk 100 to collect radiation passing through the biosensor disk 100.

In the embodiment of the disk system 200 shown in FIG. 2, the quarter wave plate 218 takes the linearly polarized collimated radiation 216 and emits circularly polarized radiation 219. The quarter wave plate 218 is oriented such that the optical axis of the quarter wave plate 218 is offset by 45 degrees from incidence of the linearly polarized collimated radiation 216.

The circularly polarized radiation 219 is directed toward a focusing lens 221. Output focused radiation 222 from the focusing lens 221 shines on the top surface 140 of the biosensor disk 100. The material that forms the top surface 140 of the biosensor disk 100 further focuses the focused circularly polarized radiation 222 onto a spot 250 on a specific physical track 112. The spot 250 is approximately circular or oval in shape and approximates the shape of the intersection of a cone by a plane perpendicular to the cone's axis. In one embodiment of the disk system 200 adapted for CD media, the diameter of the spot 250 at the level of the physical track 112 is about 2.1 µm. In another embodiment of the disk system 200 adapted for DVD media, the diameter of the spot 250 at the level of the physical track 112 is about 1.3 µm or 0.6 µm. In yet other embodiments of the disk system 200, the diameter of the spot 250 of focused radiation 222 at the level inside the biosensor disk 100 is selected to maximize the signal from the detector chamber 130.

The vertical distance between the lens 221 and the top surface 140 of the biosensor disk 100 is controlled by a lens positioner 220. The lens positioner 220 in the embodiment of the disk system 200, shown in FIG. 2, focuses the focused radiation 222. In this embodiment of the disk system 200, the lens positioner 220 changes the focus point by as much as 0.5 mm during operation. The positioning drive moves the lens 221 up and down vertically in response to errors detected at the detector 240 due to changes in the circularity of the beam at the detector 240 when the focused radiation 222 is improperly focused due to the circular nature of the lens 221. In other embodiments of the disk system 200, the lens 221 remains substantially fixed relative to the top surface 140 of the biosensor disk 100. In yet another embodiment of the disk system 220, the position of the lens 221 relative to the top surface 140 of the biosensor disk 100 is actively controlled to maximize the spot 250 size relative to the detector chambers 130 and physical track 112 passing under the point where the focused radiation 222 is focused.

The surface (not explicitly shown in the embodiment depicted FIG. 2) of the physical track 112 in the embodiment shown is a reflective surface 340, as illustrated on FIG. 3a, 3b. The reflective surface 340 causes the incident focused radiation 222 on the spot 250 to be substantially reflected back as reflected radiation 224 toward the lens 221. The reflected radiation 224 passes through the lens 221. In the embodiment shown, the lens 221 is a circular lens adapted such that as the lens 221 is out of focus with the physical track 112, the circularity of the reflected radiation 224 is distorted into an oval shaped beam that is detected at the radiation detector 240 to provide a feedback signal to the lens positioner 220. After passing through the lens 221, the reflected radiation 224 passed in through the quarter wave plate 218 in the opposite direction from the linearly polarized collimated radiation 216. The reflected radiation 224 after passing through the quarter wave plate 218 is then linearly polarized at 90 degrees and passed through the polarizing prism 214 to be directed as polarized reflected radiation 226 directed toward a detector lens 228. The detector lens 228 creates focused reflected radiation 230 that is directed toward the radiation detector 240. The focused reflected radiation 230 falls on the radiation detector 240 as a reflected spot 252 that is correlated to the reflected radiation 224 from the spot 250. An alternative embodiment of the disk system 200 eliminates the detector lens 228 and instead directly receives the polarized reflected radiation 226 on the radiation detector 240.

The radiation detector 240 in the embodiment shown in FIG. 2 is comprised of four separate radiation detectors 242, 244, 246, and 248. The four detectors are arranged in a square matrix with an upper left detector 242, an upper right detector 244, a lower left detector 248 and a lower right detector 246. The radiation detector 240 converts the incident radiation falling on itself into a signal, most commonly an analog electronic signal corresponding to the amount of reflected radiation falling on the reflected spot 252. The differential signals from the separate detectors provide feedback for tracking both the distance of the lens 221 over the top surface 140 of the biosensor disk 100 as well as the radial track position 270 of the lens 221 relative to the physical track 112 of the continuous data spiral 110. The radial track position 270 provides a means for indicating which physical track 112 of the biosensor disk 100 that the spot 250 is focused on. The lens 221 is properly focused on the physical track 112 at the proper distance from the top surface 140 when the output of all the detectors 242, 244, 246, and 248 is substantially the same after steady state offsets are removed from the signal. Differences in the output of the different detectors 242, 244, 246, and 248 provide an estimate of whether or not the lens 221 is tracking the proper radial track position 270 or the proper position of the lens 221 relative the surface of the biosensor disk 100. In another embodiment, the radiation detector 240 is a single detector that does not provide differential output. In still other embodiments, the radiation detector 240 is a multi-element radiation detector with more than four detector elements, including a charged coupled device (CCD) or complimentary metal oxide sensor (CMOS) or other imaging detector with greater numbers of radiation detector elements that provide a greater resolution estimate of the overall position, shape or geometry of the reflected spot 252 and strength of the reflected spot 252.

The lens 221 moves along a radial track 270 in order to track the focused radiation 222 on the top surface 140 of the biosensor disk 100 along the continuous data spiral 110. The movement of the lens 221 along the radial track 270 is accomplished by a linear motion carriage coupled with rotary electric motor, not shown in FIG. 2. The rotation of the electric motor causes the linear motion carriage to move back and forth along the radial track 270, thereby allowing the lens 221 to focus on a specific portion, or physical track 112 of the continuous data track 110. In one embodiment of the disk system 200, the entire radiation emitter and detection system 268 moves on the same linear motion carriage as the lens 221. In yet another embodiment, the linear motion carriage is a direct drive linear electric motor. Other mechanisms and means of moving the lens 221 or the entire radiation emitter and detection system 268 along the radial data path 270 are available to one of ordinary skill in the art.

The biosensor disk 100 is spun by a disk rotation system 266 comprising a rotary motor 260, with a shaft 262 and a hub 264. The center hole 102 of the biosensor disk 100 is adapted to mate with the hub 264. When the center hole 102 is mounted on the hub 264 the amount of rotational slipping between the biosensor disk 100 and the hub 264 is minimized. The rotation of the shaft 262 in the direction A by the rotary motor 260 thus rotates the hub 242 in the direction A and urges the biosensor disk 100 to rotate in response, also in the direction A. The rotational velocity of the rotary motor 260 is controlled by the input signal to the motor. In the embodiment shown in FIG. 2, the rotational velocity of the rotary motor 260 remains constant. In other embodiments, the rotational velocity of the rotary motor 260 is controlled to maintain a constant linear velocity of the physical track 112 over the lens 221. In still other embodiments, the rotary motor 260 changes velocity based on the quality of information being read and the amount of errors being generated at the radiation detector 240. The combination of the rotation of the biosensor disk 100 and the movement of the lens 221 enables the focused radiation 222 to be directed at and the reflected radiation 224 received from the biosensor disk 100 from substantially any point along the continuous data spiral 110 encoded on the biosensor disk 100. The disk system 200 is thus capable of reading data from across the entire continuous data spiral 110 of the biosensor disk 100.

Non-Prismatic Disk System

Another embodiment of the disk system 200, not shown, eliminates the polarizing prism 214 from the configuration of the entire radiation emitter and detection system 268. Instead the radiation emitter 202 and associated lens and filters are focused directly on the surface of the biosensor disk 100, typically at an angle. A second lens (not shown) receives the reflected radiation and focuses it on a radiation detector 240. The non-prismatic disk system eliminates some of the need for filtering and polarizing the radiation for reading the biosensor disk 100, thereby reducing the number of components in the optical path and potentially increasing the overall energy transferred from the radiation emitter 202 to the spot 250.

Linear Disk System

In another embodiment, the disk system 200 eliminates the polarizing prism 214 from the configuration of the entire radiation emitter and detection system 268. In this another embodiment, the radiation emitter 202 focuses on the top surface 140 of the biosensor disk 100. The biosensor disk 100 is substantially transparent to the radiation directed to impinge on a specific spot 250 on the physical track 112, thereby allowing the radiation to pass through the other components of the biosensor disk 100 and be received by the radiation detector 240 as it emerges from the opposite side of the biosensor disk 100.

Continuous Data Spiral of Pits and Lands

Two separate embodiments of the continuous data spiral 110 are shown in FIG. 3. The first embodiment, in FIG. 3a, is an example of a continuous data spiral 110 formed as an array of pits and lands 330 formed in the substrate 310, also shown in plan view in FIG. 6. The array of pits and lands 330 are coated with a reflective surface 340 such that when the focused radiation 222 at the spot 250, the focused radiation 222 is substantially reflected from the reflective surface 340 as reflected radiation 224. The reflective surface 340 is selected by one or ordinary skill in the art to achieve the necessary reflection of the focused radiation 222 necessary for the radiation detector 240 to detect the change in the radiation due to the structures encoded on the continuous data spiral 110. In the case of the embodiments of the disk system 200 that utilize CD and DVD wavelength radiation, the reflective surface 340 is commonly constructed of silver, aluminum, gold or copper.

For the embodiment of the disk system 200 with a polarizing prism 214, the depth of the pit 302 is nominally the quarter wave distance of the focused radiation 222. The depth of the pit 302 causes destructive interference with the reflected radiation 224, thus reducing the overall intensity of the reflected radiation 224. The reduction in intensity of the reflected radiation 224 causes the radiation detector 240 to read an average decease in radiation at the reflected spot 252 that allows the disk system 200 to differentiate between a pit 302 and the lands 304.

Figure 6:
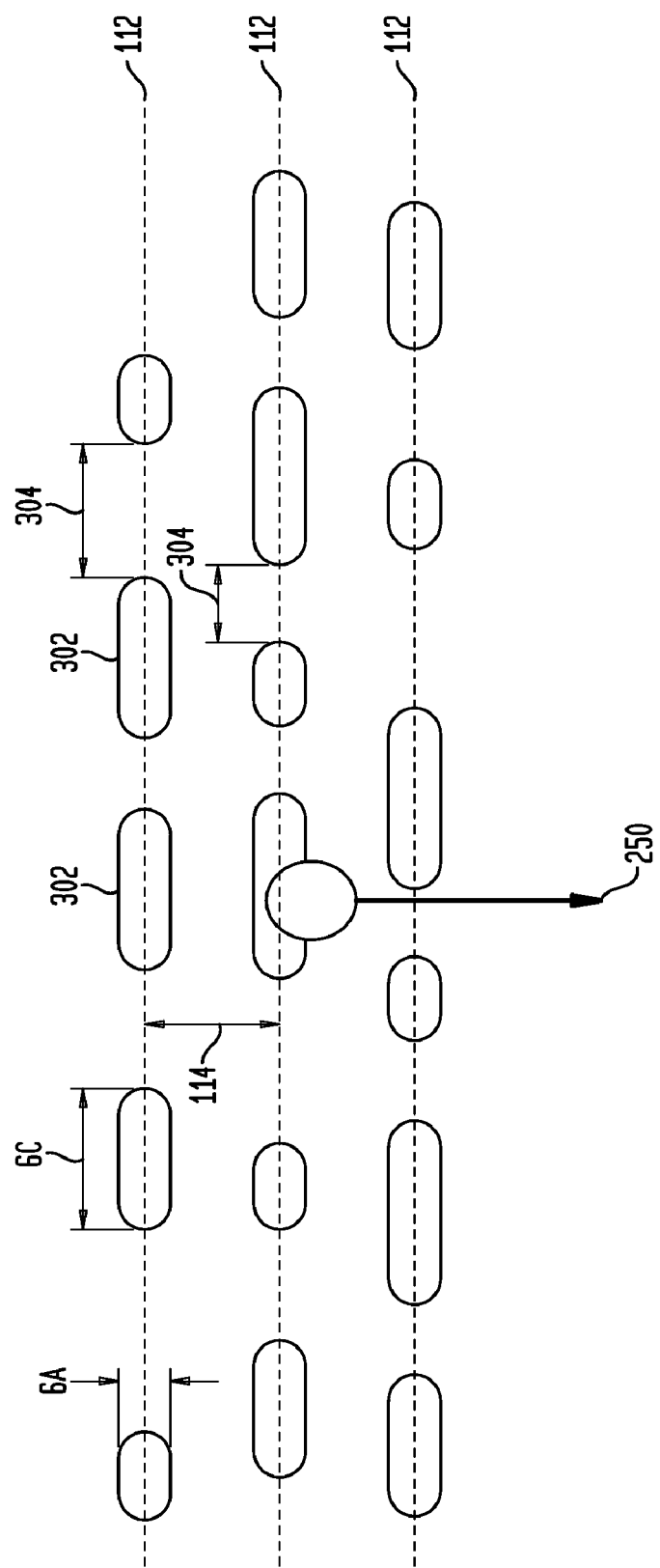
FIG. 6 is a plan view of a biosensor disk showing an array of pits and lands formed along the continuous data spiral for encoding baseline information.

As shown in FIG. 6, the pits 302 are substantially elliptical depressions formed in the surface of the substrate 310. The major axis of each elliptical depression, pit 302, is oriented along the physical track 112. Between each pit 302, both along the physical track 112 and between the physical track 112 are considered to be lands 304. The difference in height between pits 302 and lands 304 cause the intensity of the reflected radiation 224 to vary based on whether the focused radiation 222 falling on a specific spot 250 is reflected as higher or lower intensity reflected radiation 224. The difference in intensity of the radiation provides a means for the disk system 200 to determine whether the spot 250 is falling on a pit 302 or a land 304 area of the biosensor disk 100.

For the embodiment of the disk system 200 with a non-prismatic radiation source and sensor, the difference in depth between a pit 302 and a land 304 causes the reflected radiation 224 to fall on a different portion of the radiation detector 240 due to the difference in distance between the point of reflection, defined by the spot 250 falling on the reflected surface 340 in the area of a pit 302 versus a land 304. For the linear disk system 200, the signal difference in depth between a pit 302 or a land 304 is achieved through the relative transmissivity of the substrate 310 material to the focused radiation 222. In an alternative embodiment, the reflective surface 340 is replaced by a substantially non-reflective and non-transmissive material. This reflective surface 340 is then patterned using multiple techniques including, but not limited to scribing, laser ablation, photolithography, and other techniques necessary to create voids in the non-reflective and non-transmissive material located where the reflective surface 340 is nominally placed in order to create detectable high and low points for the radiation detector.

The embodiment of the biosensor disk 100 shown in FIG. 3, has a protective substrate 312 covering over the reflective material 340 on the backside 342 of the biosensor disk 100 to protect the reflective material 340 from accidental damage.

Substrate Materials and Fabrication

In the embodiment of the permanently formed continuous data spiral 110 shown in FIG. 3a and in FIG. 6, the pits 302 and lands 304 are formed when the biosensor disk 100 is initially fabricated, typically by pressing or casting of the substrate 310. The substrate 310 in the case of the permanently formed continuous data spiral 110 is comprised of a series of depressions or pits 302 surrounded by the other surface of the face of the substrate 310, commonly called lands 304. A top view of three physical tracks 112 of a continuous data spiral 110 with permanently recorded information in the form of an array 330 of pits 302 and lands 304 is shown in FIG. 6. The substrate 310 of the embodiment of the biosensor disk 100 shown in FIG. 6 is typically a polycarbonate material.

Other substrate materials can be used for the biosensor disk 100 including other polymer materials or other metallic and non-metallic materials. In one embodiment, the substrate 310 of the biosensor disk 100 is formed from polystyrene. In another embodiment of the biosensor disk 100, the polycarbonate material is replaced by a single-crystal silicon. The single crystal silicon enables the pits to be formed using common microelectronic and micro fabrication techniques, providing a high degree of accuracy and repeatability from biosensor disk 100 to biosensor disk 100. In still other embodiments, the single crystal silicon is replaced by other substrate materials, including but not limited to gallium arsenide, silicon carbide, silicon-on-insulator (SOI), and silicon nitride. All of these materials can be processed using common microelectronic fabrication techniques using techniques such as photolithography, sputtering, chemical vapor deposition, deep reactive ion etching, wet and dry etching, and other wafer fabrication techniques, as would be generally understood by one of ordinary skill in the art, to create a combination of detector chambers 130 and pits 302 and lands 304 necessary to encode the baseline data 902.

In another embodiment, the biosensor disk 100 has a polycarbonate portion and a silicon crystal potion. In this embodiment, the majority of the biosensor disk 100 is made of polycarbonate while the analyte detector region 120 is made of a higher melting point material, such as SiO2 (silicone dioxide). This has the advantage of allowing the majority of the disk to be produced inexpensively, while allowing the analyte detector region 120 to be constructed of a more durable material that can withstand high temperature processes such as those commonly used in microelectronic fabrication as described above.

The selection of specific substrate materials is guided by a number of factors, including compatibility with the desired analytes, physical strength, the ability to create alternative shapes, the type of radiation necessary to discriminate between detector ligands 380 and bound detector ligands 480 that are affixed to an analyte 960. Other factors that impact the selection of materials include materials compatibility between different elements of the physical structure and the ability to create the continuous data spiral 110 in the material at the resolutions necessary to accommodate the desired detector chambers 130.

The embodiment shown in FIG. 6 is configured with pits 302 and lands 304 sized for an unmodified CD reader. In this embodiment, each of the pits 302 has a pit width 6 A of approximately 0.5 μm. The major axis of each pit 302 is oriented along the physical track 112. The pit length 6C is based on the information encoded in the substrate at that specific location (see description below) and ranges from about 278 nm to about 3560 nm. The spaces outside of the pits 302 are called land 304.

Continuous Data Spiral Formed from Writeable Materials

The second embodiment of recoding the baseline information or baseline data 902 on the continuous data spiral 110 is shown in FIG. 3b. This second embodiment uses writeable materials that enable the baseline data 902 to be written to the biosensor disk 100 after the biosensor disk 100 has been fabricated. The biosensor disk 100 is formed with a continuous pregroove 308 along the continuous data spiral 110. The continuous pregroove 308 is formed in the substrate 310 using the similar techniques as used for forming the pits 302 and lands 304 of FIG. 3a. The continuous pregroove 308 in the embodiment shown is a groove with a width of 0.6 μm.

The continuous pregroove 308 has a radial wobble its path with at 22.05 kHz. The wobble is frequency modulated with a 1 kHz time code that provides an Absolute Time In Pregroove (ATIP). The radial wobble and the ATIP frequency modulate provide additional information that the radiation detector 240 can use to control the position of the spot 250 on the surface of the biosensor disk 100.

The continuous pre-groove is coated in this embodiment with a writeable material 314. The writeable material 314 in the embodiment in FIG. 3b is an ablative material that absorbs focused radiation 222 directed at the writeable material 314. When the radiation emitter 202 is emitting radiation in a high power mode, the writeable material 314 is heated up and upon cooling incurs a local phase change from one phase, typically an amorphous phase as deposited on the substrate 310, to a second phase typically polycrystalline in form. The transmissivity of the writeable material 314 to the focused radiation 222 changes from the amorphous state to the crystalline state of the writeable material 314. The writeable material 314 is coated with a reflective layer 340 that reflected the focused radiation 222 back. The change in the amorphous state of the writeable material 314 thus modulates the light passing through the writeable layer 314. The use of heat from radiation to change the phase of the materials used in the writeable layer 314 enables the writeable layer 314 to be written with information after the biosensor disk 100 is manufactured. This flexibility enables the biosensor disk 100 to have the baseline data 902 encoded in the continuous data spiral 110 adapted for the detection of specific ligands based on the type of detector chambers 130 being used.

In alternative embodiments, the writeable material 314 is a phase change material that can be reversed such that the portion of the writeable material 314 under the spot 250 can be selectively changed between two different phases with two different transmissivity levels for both encoding information and clearing information from the continuous data spiral 110. The writeable material 314 used in a linear disk system 200 can be used without a reflective surface 340.

There are a number of different writeable materials 314 and reflective materials 340 that can be used to create the writeable layer. In the embodiments suitable for encoding the baseline data 902 for a CD or DVD there are multiple materials used for the writeable layer, including but not limited to the following writeable materials 314: Cyanine, Pthalocyanine, Azo, and Formazan. Other combinations are known to those or ordinary skill in the art, and other combinations can be used that are adapted to the use of different wavelengths of radiation.

Protected Detection Chamber Above Continuous Data Track

The embodiment of the biosensor disk 300 with protected detector chambers 130 shown in FIGS. 3a and 3b has a detector substrate 350 placed above and integrated with the substrate 310. The biosensor disk 300 with protected detector chambers 130 shown in FIGS. 3a and 3b is shown as an exploded assembly for easy viewing. The individual elements in the assembled biosensor disk 300 with protected detector chambers 130 physically abut each other when they are assembled in the direction 3A. The detector substrate 350 has detector chambers 130 formed in the detector substrate 350. The detector chambers 130 are formed in the detector substrate 350 using a multitude of processes known to those of ordinary skill in the art, including the casting or pressing process used to form the pits 302 and lands 304 in the substrate 310. The detector substrate 350 is fabricated from a variety of different materials, ranging from polymers such as polycarbonate and non-metallic materials like silicon through metallic materials. The selection of the detector substrate 350 by one of ordinary skill in the art is based on a number of factors, including but not limited to, the relative materials match between the substrate 310 and the detector substrate 350, the ability to glue or otherwise join the substrate 310 to the detector substrate 350 in those applications that require a single element system, the relative transmissivity of the material relative to the focused radiation 222, and other factors including the ability of the detector substrate 350 to bind to detector ligands 380, thereby forming bound detector ligands 480, and being substantially unreactive to the analyte 960 and or other materials present in the sample 950.

The detector chambers 130 formed in the detector substrate 350 are adapted to maximize the change in the reflected radiation 224 detected at the radiation detector 240 relative to the baseline data 902 encoded on the substrate 310. The detector ligands 380 are placed in the detector chamber 130 of the detector substrate 350. The detector ligands 380 are adapted to bind, accept, or otherwise capture specific analytes 960 found in the sample 950 to be analyzed. When the detector ligands 380 bind to the analyte 960, they form bound detector ligands 480. The bound detector ligands 480 have a lower radiation transmissivity properties as compared to the detector ligands 380, thereby changing the signal received by the disk system 200. The process for attaching the detector ligands 380 to a substrates and the selection of detector ligands 380 that will form bound detector ligands 480 with specific analytes 960, is described in greater detail below.

In this embodiment, an elongated channel or fluidic passage 360 is also formed in the substrate (shown as hidden lines). The fluidic passage 360 enables a sample 950 to be analyzed to be inserted at the entrance to the fluidic passage 360 and then travel along the fluidic passage 360 to the detector chamber 130 in order to be exposed to the detector ligands 380. In one embodiment, the fluidic passage 360 is formed between the detector substrate 350 and the reflective surface 340. In another embodiment, the fluidic passage 360 is formed fully inside the detector substrate 350 by either integrating multiple detector substrates 350 together or by burrowing a channel directly through the detector substrate 350. Additional fluidic control elements, as described below, are integrated within the fluidic passage 360 and detector chamber 130 areas in other embodiments to control the flow of the sample 950 through the biosensor disk 300.

In the embodiment depicted in FIGS. 3a and 3b, the detector substrate 360 is bound to the substrate during the fabrication process of the biosensor disk 300 with protected detector chambers 130. This creates a sealed system, whereby the detector ligands 380 are protected by the substrate 310 and the detector substrate 350. Prior to use, if the baseline data 902 has not been encoded on the continuous data spiral 110, the biosensor disk 300 with detector ligands 380 can be encoded immediately prior to use after the detector substrate 350 has been affixed to the substrate 310. Alternatively, for biosensors disks 300 with pre-encoded continuous data spirals 110 and for writeable biosensor disks 300 with the writeable material 314 on the substrate 310, these disks are pre-encoded with baseline data 902 adapted to maximize the changes recorded by the radiation detector 240 and interpreted by the interpreter.

The sample 950 and the analyte 960 are placed into the embodiment of the biosensor disk 300 with the detector substrate 350 affixed to the substrate 310. The sample 950 with the analyte 960 contained within, flow through the fluidic passages 360 to the detector chamber 130. In an alternative embodiment, the detector substrate 350 is separate from the substrate 310. In one embodiment, the detector substrate 350 is emersed as a single unit into one or more substances, including being placed in preparatory fluids prior to being exposed to the sample 950. The detector substrate 350 is then processed in order to maximize the adhesion of the analyte 960 to the detector ligands 380. After processing of the detector substrate 350 separately from the substrate 310, the detector substrate 350 is affixed or joined to the substrate 310. In one embodiment, the detector substrate 350 fits into physical mating structures that help orient and lock the detector substrate 350 in radial relation to the substrate 310. These physical mating structures can include, but are not limited to, tongue and grooves, slot and tabs, spoke and channel structures, and other unique geometries capable of orienting the detector substrate 350 relative to the substrate 310. In yet another embodiment, the detector substrate 350 is affixed to the substrate 310 with an adhesive compound placed between the detector substrate 350 and the substrate 310. The adhesive compound could be used independently or in conjunction with one of the physical mating structures described above. In still another embodiment, the detector substrate 350 is held against the substrate 310 using an external clamping structure, such as a clamping ring.

Exposed Detection Chamber Above Continuous Data Track

FIG. 4 depicts an alternative embodiment that places the detector chamber 130 on the exposed top surface 140 of the biosensor disk 400 with exposed detector chambers 130. The biosensor disk 400 with exposed detection chambers 130 shown in FIG. 4 is shown as an exploded assembly for easy viewing. The individual elements in the assembled biosensor disk 400 with exposed detection chambers 130 physically abut each other when they are assembled in the direction 4A.

The detector substrate 350 for the biosensor disk 400 with exposed detector chambers 130 is fabricated using the same fundamental fabrication and materials approaches discussed in the fabrication of the biosensor disk 300 with protected detector chambers 130 above. Detector ligands 380 are similarly attached to detector chambers 130. The exposed detector substrate 350 is affixed to the substrate 310, in this case shown with a continuous pregroove 308 and writeable material 314 in addition to the reflective layer 340 and protective substrate 312, either prior to or after exposure to the sample 950. The detector substrate 350 is affixed to the substrate 310 using the similar techniques as well.

Integrated Detection Chamber Formed with Continuous Data Track

Figure 5:
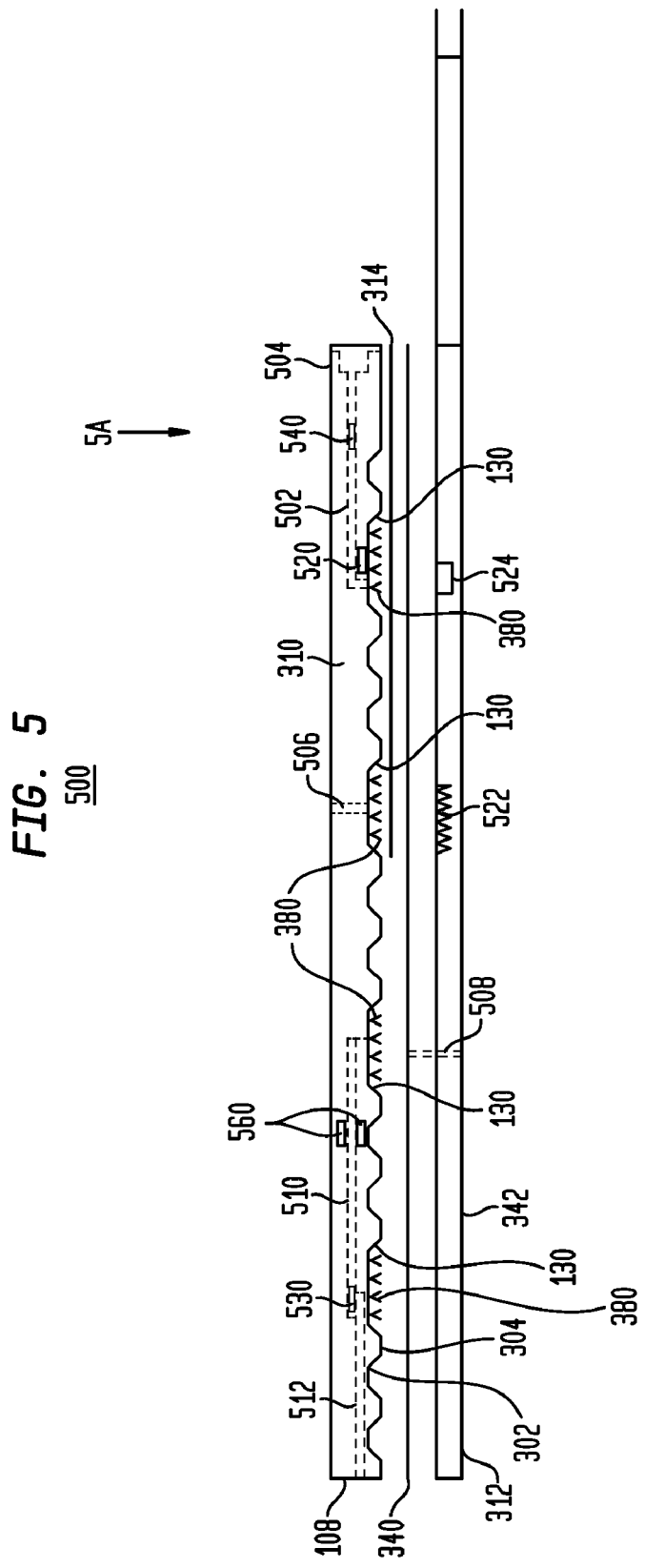
FIG. 5 is a cross-sectional view of a biosensor disk of a third embodiment, wherein said detection chambers are constructed as one unitary element with the data tracks of the biosensor disk.

FIG. 5 depicts an alternative embodiment that integrates the detector chamber 130 on the substrate 310 with the continuous data spiral 110 to create a biosensor disk 500 with integrated detection chambers 130. The biosensor disk 500 with integrated detector chambers 130 shown in FIG. 5 is shown as an exploded assembly for easy viewing. The individual elements in the assembled biosensor disk 500 with exposed detection chambers 130 physically abut each other when they are assembled in the direction 5A.

The biosensor disk 500 with integrated detector chambers 130 places the detector chambers 130 on the same plane as the pits 302 and lands 304 or continuous pregroove 308 and fabricates the physical structure of the detector chambers 130 as part of the same fabrication process. The biosensor disk 500 with integrated detector chambers 130 shown in FIG. 5 includes both a continuous data spiral 110 comprised of pits 302 and lands 304 and a continuous data spiral 110 formed with a continuous pregroove 308 and writeable material 314.

The detector chambers 130 on the biosensor disk 500 are sized and adapted to appear to the disk system 200 as the equivalent to a pit 302 in the surface of the substrate 310. The detector ligands 380 are attached to the detector chambers 130 using the processes outlined below. The detector chambers 130 are in one embodiment separately covered by a thin film protective coating (not shown) to separate the detector chamber from the reflective layer 340 or the writeable material 314. In another embodiment, the detector chambers 130 are integrated with and exposed to the writeable material 314 or the reflective material 340. The substrate 310 is affixed to the reflective layer 340 or writeable material 314 and reflective layer 340 using either thermal bonding or adhesive means based on the ability of the detector ligands 380 to withstand a given process.

Microfluidic Handling

The embodiment shown in FIG. 5 depicts a variety of different microfluidic handling approaches for enabling the transport of the sample 950 to a given detector chamber 130 whereby an analyte 960 can bind with the detector ligands 380 to change the relative transmissivity of the detector chamber 130 and highlight the presence of the analyte 960 in the sample 950. The microfluidic handling approaches depicted herein are appropriate for all embodiments of the biosensor disk 100, 300, 400, 500. They are highlighted on the biosensor disk 500 with integrated detector chambers 130 for convenience only.

A detector chamber 130 is fed from an input hub chamber 504. The input hub chamber 504 occupies the central portion of the biosensor disk 500. A means is provided for a sample 950 to be input into the input hub chamber 504. The input hub chamber 504, in one embodiment, has a flexible bung enabling a syringe or other object to be pressed into the input hub chamber 504 for injecting the sample 950. In another embodiment, the input hub chamber 504 has a resealable lid or cover (not shown) that enables the input hub chamber 504 to be exposed and filled. Other means and methods of inputting a fluid into the input hub chamber 504 for distribution to the remainder of a given biosensor disk 500 are available to those of ordinary skill in the art. In the embodiment shown in FIG. 5, the biosensor disk 500 with integrated detector chambers 130 has one type of fluidic passage 360, in this case, an input hub to detector chamber connector 502 connecting the input hub chamber 504 to a detector chamber 130.

A second method of inputting the sample 950 into a detector chamber 130 is through a another type of fluidic passage 360, a top surface input passage 506. The top surface input passage 506 provides a means for accessing a detector chamber 130 through the substrate 310. The top surface input passage 506 in one embodiment is covered with a bung or similar flexible material that can be pierced by a sharp object or needle thereby allowing the sample 950 to flow into the top surface input passage 506 and the detector chamber 130. In one embodiment, the volume formed within the top surface input passage 506 and the detector chamber 130 is held at a vacuum, such that when the bung is pierced by a needle or other instrument, the sample 950 is urged into the top surface input passage 506 and the detector chamber 130.

Two microfluidic passages 360 can be combined to enable a flow of substances from the input fluidic passage 360 through the detector chamber 130 to an outlet fluidic passage 360. For example, in another embodiment, two top surface input passages 506 (only one shown for convenience) are combined such that fluid is inserted into one top surface input passage 506 while the air presently tapped within the volume formed by the detector chamber 130 and the top surface input passages 506 is displaced through the second top surface input passage 506. In yet another embodiment, the volume formed within the top surface input passage 506 and the detector chamber 130 is filled with an inert gas or fluid, such as nitrogen, argon, or distilled water, or silicone oil, selected to minimize adverse effects to the detector ligands 380 inside the detector chamber 130. A pair of top surface input passages 506 are used together with one top surface input passage 506 being used to input the sample 950 while the other top surface input passage 506 is used to exhaust the inert gas or fluid. Multiple combinations of fluidic passages 360 can be used by one of ordinary skill in the art to encourage the flow of the sample 950 through the detector chambers 130 and also in some embodiments provide an additional means of protecting the detector ligands 380 prior to use.

Yet another method of inputting a sample 950 into a detector chamber 130 is through yet another type of fluidic passage 360, a bottom surface input passage 508. The bottom surface input passage 508 passes through the protective substrate 312 and the reflective surface 340 and if present any other layers between the protective substrate 312 and the detector chamber 130, including a writeable material 314. The bottom surface input passage 508 operates in a similar manner and is configured in similar ways to other fluidic passages 360. Similarly to the other fluidic passages 360, the bottom surface input passage 508 in some embodiments is lined to isolate the sample 950 from the materials surrounding the fluidic passage 360.

Another method of transporting the sample 950 through a biosensor disk 100, and particular in the case of the biosensor disk 500 with integrated detector chambers 130 shown in FIG. 5 is yet another type of fluidic passage, an interchamber fluidic passage 510. The interchamber fluidic passage 510 enables a sample 950 and other fluids or gases present in a given volume defined by the detector chambers 130 and the fluidic passages 360 to pass from one detector chamber 130 another detector chamber 130.

The embodiment of the biosensor disk 500 with integrated detector chamber 130 shown in FIG. 5 has yet another type of fluidic passage 360, an edge exhaust passage 512. The edge exhaust passage 512 enables the release of fluids and/or gasses inside the volume of the fluidic passages 360 and the detector chambers 130 and allows their release to the outer edge 108 of the biosensor disk 100, or the biosensor disk 500 with integrated detector chambers 130, as shown in embodiment in FIG. 5.

Controlled Fluidic Mixing and Fluid Flow

In still other embodiments, the microfluidic passages 360 and the detector chambers 130 are combined with other microfluidic structures and control elements for maximizing the binding of the detector ligands 380 to the analyte 960 to form bound detector ligands 480 adapted for detection by the disk system 200. These elements include filtration blocks 540, removable barriers 530, passive heaters 520, electrophoretic elements 560, active heaters 522, and additional sensors 524.

In the embodiment shown in FIG. 5, there is a passive heater 520 placed along the underside of a detection chamber 130. The passive heater 520 is adapted to absorb the focused radiation 222 from the disk system 200 and convert the absorbed radiation to heat. The passive heater 520 is arranged in a pattern around the detector chamber 130 and relative to the continuous data spiral 110 and its baseline data 902 such that the absorbed radiation is treated as information. The disk system 200 is commanded to read the track over the passive heater 520 a number of times based on the absorbativity of the passive heater 520, the amount of heating desired in the detector chamber 130, and other factors in order to heat the detector chamber 130 in the vicinity of the passive heater 520.

This localized heating provides a means for encouraging the binding of the analyte 960 to the detector ligands 380 or in alternative processes for encouraging mixing and chemical reactions between the sample 950 and chemicals located within the detector chamber 130. In alternative embodiments, the passive heater 520 is placed in proximity to fluidic passages 360 to heat the sample 950 in the vicinity of the passive heater 520.

A filtration block 540 is placed within a fluidic passage 360, in the embodiment shown in FIG. 5, the top surface input passage 502. The filtration block 540 is formed of materials suitable for filtering the sample 950 prior to, or between exposure to different detector chambers 130 in the biosensor disk 500. A person of ordinary skill in the art will select appropriate filtration materials, including the use of multiple filtration blocks 540 in a cascade manner, to filter and prepare a given sample 950 prior to entering a detector chamber 130. Some materials used for the filtration block 540 including, but are not limited to, carbon, cellulose, ceramic, cotton, glass, ion exchange resin, metal, minerals, paper, nylon, polyethersulfone (PES), polyester, polypropylene (PP), polytetrafluoroethelyne (PTFE), polyvinylidene fluoride (PVDF), polyvinylidene chloride (PVDC), polysulfone, and sand. The filtration block 540 in one embodiment extends the full length of a fluidic passage 360 and the sample 950 must pass through the filter block 540 to move through the fluidic passage 360. In other embodiments, the filtration block 540 partially occludes the fluidic passage 360.

The filtration block 540 in other embodiments are impregnated with other chemicals suitable for pre-treating the sample 950 prior to exposure to the detector ligands 130 contained within the detector chambers 130. The selection of chemicals for pre-treatment of the sample 950 is selected according to the types of detector ligands 380 and analyte 960 being used.

In still other embodiments, the filtration block 540 merely slows the flow of the sample 950 through the biosensor disk 500 in order to control the amount of time the sample 950 spends inside a given detector chamber 130 or fluidic passage 360 prior to passing to the next element on the biosensor disk 500.

In another embodiment, the fluidic passage 360 is temporarily blocked using a removable barrier 530, shown on the biosensor sensor disk 500 with integrated detector chambers 130 in FIG. 5. The removable barrier 530 is constructed of a material that absorbs the focused radiation 222 from the disk system 200 and selectively weakens and breaks or vaporizes such that flow of the samples 950 can be controlled from a state of no flow (removable barrier 530 intact) to a state where flow is allowed (removable barrier 530 is breached) using only the focused radiation 222 from the disk system 200. In yet another embodiment, the removable barrier 530 is positioned in proximity to either a passive heater 520 or an active heater 522 and the localized heating from those elements removes the removable barrier 530.

Active heaters 522 and sensors 524 can be operated using batteries either placed within or on the biosensor disk 500, or alternatively powered by the disk system 200 through either direct electrical connections in the hub 264 or via radiation provided by the disk system 200 to a receiver located on the biosensor disk 500. Active heaters 522 provide similar localized heating of the sample 950 or various portions of the detector chamber 130 and fluidic passages 360 to urge flow, encourage chemical reactions and binding to detector ligands 380, and otherwise control the flow of the sample 950 through the system. Additional sensors 524 can be integrated with other active elements, such as the active heaters 522 or passive heaters 520 to provide additional capabilities such as temperature regulation.

There are multiple means for urging a sample 950 to pass through a given biosensor disk 500 with fluidic passages 360 and into or through a detector chamber 130. One means is the use of pressure applied to the sample 950 that urges the sample 950 to flow and occupy the fluidic passages 360 and detector chambers 130.

A second means is the use of the centrifugal force generated by the spinning of the biosensor disk 500 in the disk system 200. The spinning of the biosensor disk 500 generates a body force on the sample 950 urging the sample 950 to flow outward from the center or hub 264 toward the outer edge 108. Another means for urging the sample 950 to flow through the biosensor disk 500, is the use of selective heating by a passive heater 520 or active heater 520 of the sample 950 in the fluidic passage 360. The selective heating of some of the sample 950 within the fluidic passage 360 provides a motive force for urging the sample 950 through the fluidic passages 360 and detector chambers 130 using buoyant or thermally driven forces. The selective heating can be augmented by various means of cooling the sample in order to maximize the thermal gradients and promote the thermally driven flow.

In yet another means, the fluidic passage 360 in the biosensor disk 500 are configured to operate like a centrifuge to separate, mix, or even process the analyte in order to maximize the response of the biosensor system 210. The biosensor disk 500 can easily exceed 180 rev/second while being read using most commercial CD disk systems 200. The rotational velocity of the biosensor disk 500 can be used to move the sample 950 along the fluid passages 360 and the detector chambers 130 through the body forces applied to the sample 950 caused by the rotation of the biosensor disk 500 in the disk system 200. The rotation of the biosensor disk 500 is controlled by the structure of the information encoded on the biosensor disk 500 or, in other embodiments, through direct control of the rotation system 266. In one embodiment, the sample 950 is placed in the center of the biosensor disk 500 within the input hub chamber 504. The input hub chamber 504 in another embodiment also comprises a chemical digestion chamber with chemicals adapted to free the DNA or RNA or other proteins of a bacterial spore sample by chemical digestion of the basal layer and other membranes. The biosensor disk 500 is rotated in some embodiments to encourage the operation of the chemical digestion chamber located in the input hub chamber 504. After the chemical digestion process is complete, the biosensor disk 500 with input chamber hub 504 is spun in order to separate and urge the sample 950 toward fluidic passages 360 to the detector chambers 130. The detector ligands 380 located within the detector chambers 130 then bind to the analyte 960 contained within the sample 950 to form bound detector ligands 480.

Still another means for urging the movement of the sample 950 is the use of an electrophoretic element 560 that creates an electric field over a fluidic passage 360, as shown in the embodiment in FIG. 5. The electric field created by the electrophoretic element 560 urges both the separation of molecules within the sample 950 and the movement of the sample 950 through the passage due to the urge exerted by the electronic field on the sample 950 and the constituent chemicals and materials within the sample 950. The electrophoretic element 560 in some embodiments is combined with a filtration block 540 to urge specific constituent chemicals and materials in the sample 950, including in some embodiments the analyte 960, to separate.

All of these means for urging the sample 950 to move through the fluidic passages 360 into and through the detector chambers 130 can be used either independently, or in combination by one of ordinary skill in the art to control the flow of the sample 950 through the biosensor disk 500.

Process for Interrogating a Biosensor Disk with Computer

Figure 7:
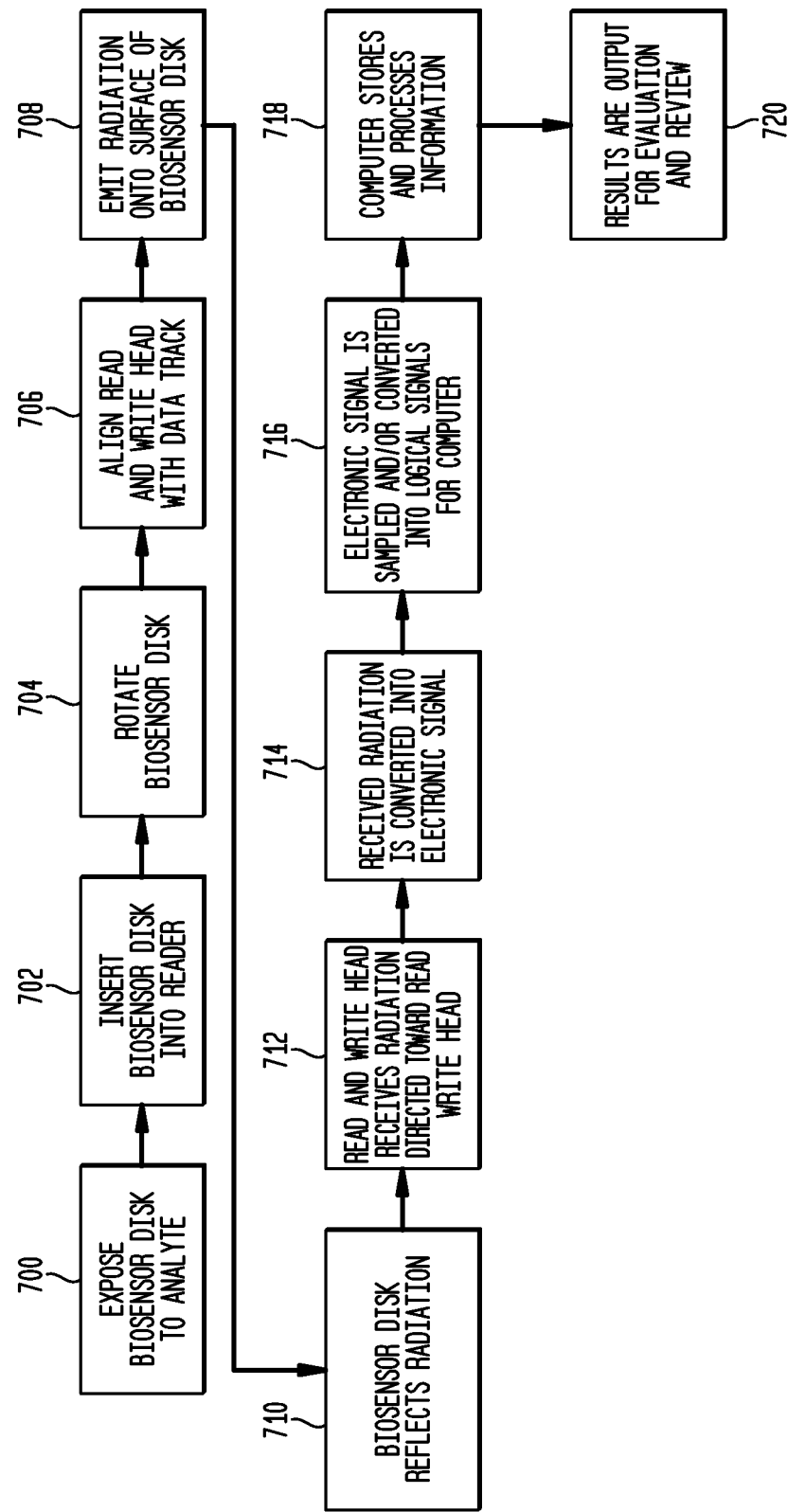
FIG. 7 is a logical block diagram of one embodiment of the system, wherein the results of the biosensor are processed using a computer.

FIG. 7 provides a flow diagram outlining the process for using a biosensor system 210 to detect the presence of a specific analyte 960 by interrogating a biosensor disk 100 that has been exposed to a sample 950. The biosensor disk 100 has baseline data 902 encoded on the continuous data spiral 110. First, the biosensor disk 100 is exposed 700 to the sample 950 containing the analyte 960. The biosensor disk 100 exposed 700 to the analyte 960 is processed if necessary to encourage the detector ligands 380 to bind to the analyte 960 and thereby form bound detector ligands 480. After the biosensor disk 100 is exposed 700, it is inserted 702 into the disk system 200, and nominally mated to the hub 264. The inserted 702 biosensor disk 100 mated to the hub 264 of the disk system 200. The hub 264 is rotatably connected to the rotary motor 264 thereby enabling the rotation 704 of the biosensor disk by the disk system 200. The rotational speed of the biosensor disk 100 is controlled by the disk system 200.

After the biosensor disk 100 is rotating 704, the disk system 200 aligns 706 the read write head or focusing lens 221 with the continuous data spiral 110 encoded on the substrate 310 of the biosensor disk 100. The aligned 706 focusing lens 221 emits 708 focused radiation 222 onto the surface of the biosensor disk 100. The emitted 708 focused radiation 222 penetrates the substrate 310 of the biosensor disk 100 to focus on a spot 250. The focused radiation 222 is reflected 710 back toward the focusing lens 221 as reflected radiation 224. The reflected radiation 224 is received 712 by the focusing lens 221 and directed toward the radiation sensor 240. The radiation sensor 240 then converts 716 the reflected radiation 224 into an electronic signal. The electronic signal is then sampled 716 by a computer at a predefined frequency. The sampling 716 process in one embodiment is comprised of thresholding the electronic signal converted 714 by the radiation sensor 240 to create a binary representation of the signal, i.e. either a zero or a one. In another embodiment the electronic signal is sampled 716 using a multi-bit analog to digital converter (ADC) to create a multi-bit, binary representation of the signal that corresponds to the intensity of the sampled 716 electronic signal.

In one embodiment, each separate radiation detector: upper left detector 242, upper right detector 244, lower right detector 246, and the lower left detector 248 of the radiation detector 240 are averaged together as they are converted 714 and the aggregate electronic signal is then sampled 716. In another embodiment, the electronic signal is converted 714 from each of the separate radiation detectors 242, 244, 246, and 248 into four channels. The electronic signal is sampled 716 on each of the four separate channels and converted using either a thresholding process or a multi-bit analog to digital converter.

After the information reflected 710 from the biosensor disk 100 is sampled 716, a computer stores and processes 718 the information. The storage and processing 718 includes matching of the sampled information to the time interval embedded within the baseline data 902 encoded within the continuous data spiral 110 of the biosensor disk 100. Additional processing is performed as outlined below to interpret the information contained based on the reflected radiation 224 from the biosensor disk 100 comprising information from the detector ligands 380, bound detector ligands 480, and pits 302 and lands 304 of one embodiment or the selective phase change of the writeable material 314 in another embodiment, coupled with the reflectively surface 340. In the case of a linear disk system 200, there is no reflective surface 340. The stored and processed 718 results are then output 720 for evaluation and review in graphical, audio, or tactile means.

Process for Interrogating a Biosensor Disk with Standard Audio Player

Figure 8:
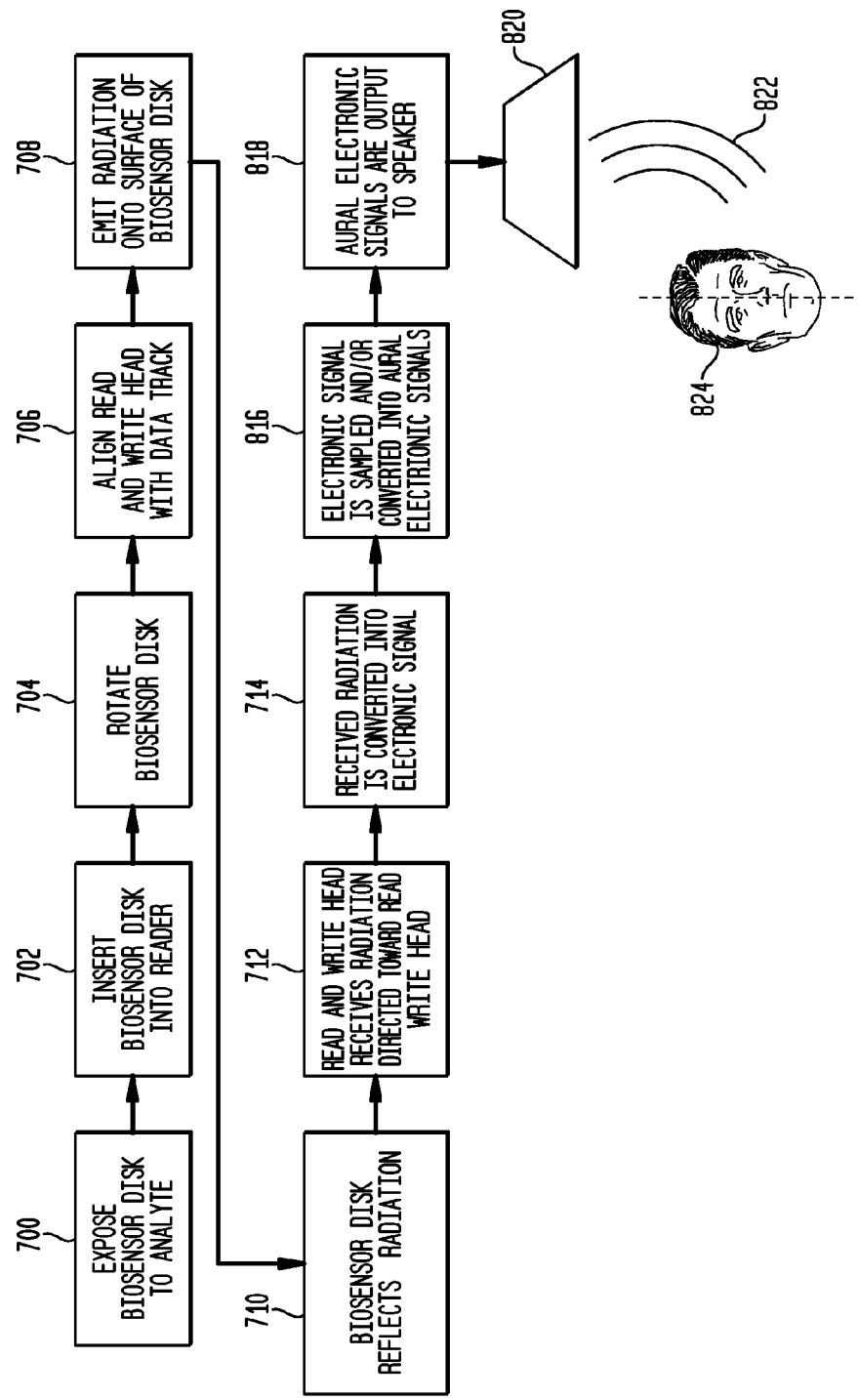
FIG. 8 is a logical block diagram of another embodiment of the system, wherein the results of the biosensor are processed using the human ear.

FIG. 8 provides flow diagram highlighting the process for using a biosensor system 210, comprising a standard consumer audio device, such as a CD player, to detect the presence of one or more analytes 960 by interrogating a biosensor disk 100 that has been exposed 700 to a sample 950. The biosensor disk 100 in this embodiment has baseline information encoded on the substrate 310, in either the pits 302 and lands 304 or in the writeable materials 314 that corresponds to audio signals in digital form suitable for use by a standard consumer audio device. The same steps are used for interrogating the biosensor disk 100 with the standard consumer audio device as used with computer from the initial steps of exposing 700 the biosensor disk 100 to the sample 950 which may or may not contain the analyte 960 through converting 714 the reflected radiation 224 to an electronic signal. The electronic signal is sampled 816 using a thresholding system to create a stream of zeros and ones or raw binary information. The raw binary information corresponds to the relative reflectivity of the biosensor disk 100 under the spot 250 at the time of reading. While converting 816 the electrical signal, the raw binary information is typically buffered to enable correlation of the raw binary information with the proper sampling frequency based on the rate of information encoded on the continuous data track.

Part of converting 816 the electrical signal into an aural electronic signal is the conversion of the raw binary information to digital data. The baseline data 902 stored on the continuous data spiral 110 of the biosensor disk 100 is encoded using eight to fourteen (EFM) modulation. The EFM system is described in greater detail below, has the practical effect of the standard is to map the raw binary information read from the surface of the continuous data spiral 110 as 14-bit information into 8-bit digital words corresponding to upper and lower bytes of an audio signal which provides some protection against single-bit errors because only 256 of the 16,384 combination are allowable. The 8-bit digital words are reconstructed into audio digital signals using the data conversion standards described in greater detail below. The bound detector ligands 480 effect the digital audio signal while being converted 816 in multiple ways, including the introduction of unrecoverable errors E32 errors and by changing the 8-bit digital word coming from the conversion 816. These E32 errors and modifications to the 8-bit digital words arising due to the effect of the bound detector ligands 480 on the transmission of the focused radiation 222 through the detector chamber 130 impacts the converted 816 aural electronic signals. The aural electronic signals are output 818 using a combination of digital to analog converters (DAC) and amplifiers as an analog waveform corresponding to the reflected radiation 224 received from the biosensor disk 100 as a function of the baseline data 902 encoded in the continuous data spiral 110 coupled to the effect of the bound detector ligands 480. The aural electronic signals are fed 820 to a speaker that converts the electronic input to audio waves. The audio waves travel through the air 822 and are heard 824. In the case of the a human being, the audio waves are heard 824, and the effect of the bound detector ligands 480 manifests as a distinct individual or series of pops, interruptions, frequency shifts, or other disturbances in the signal. In some embodiments, the detection of the analyte 960 in the sample 950 results in the consumer audio player being unable to play the biosensor disk 100 and displaying an error.

Process for Integrating Separate Detector Substrate with Substrate

Figure 9:
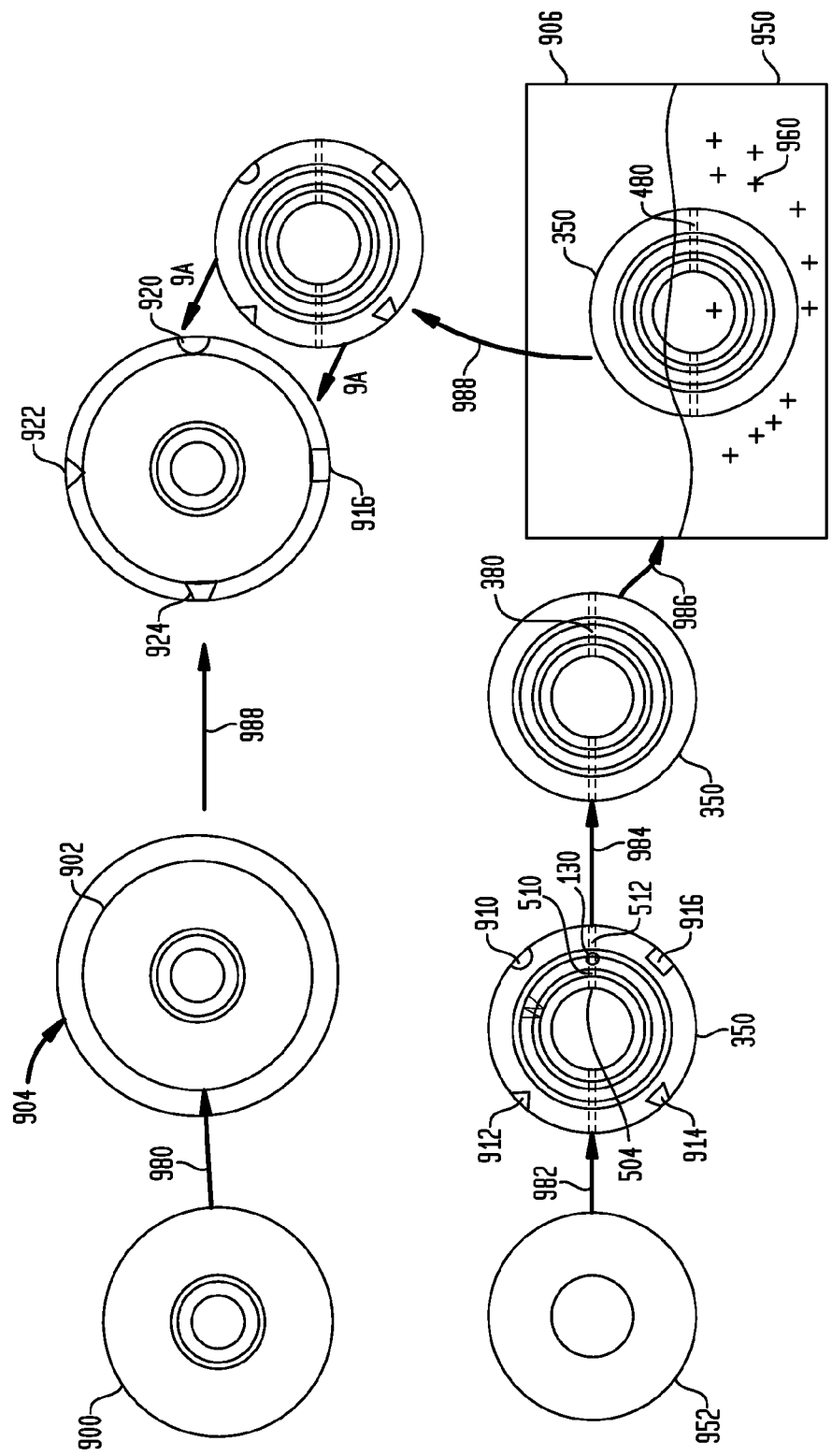
FIG. 9 is a block diagram depicting the steps necessary to create a biosensor disk of the first embodiment with a single analyte detector ligand.
Figure 10:
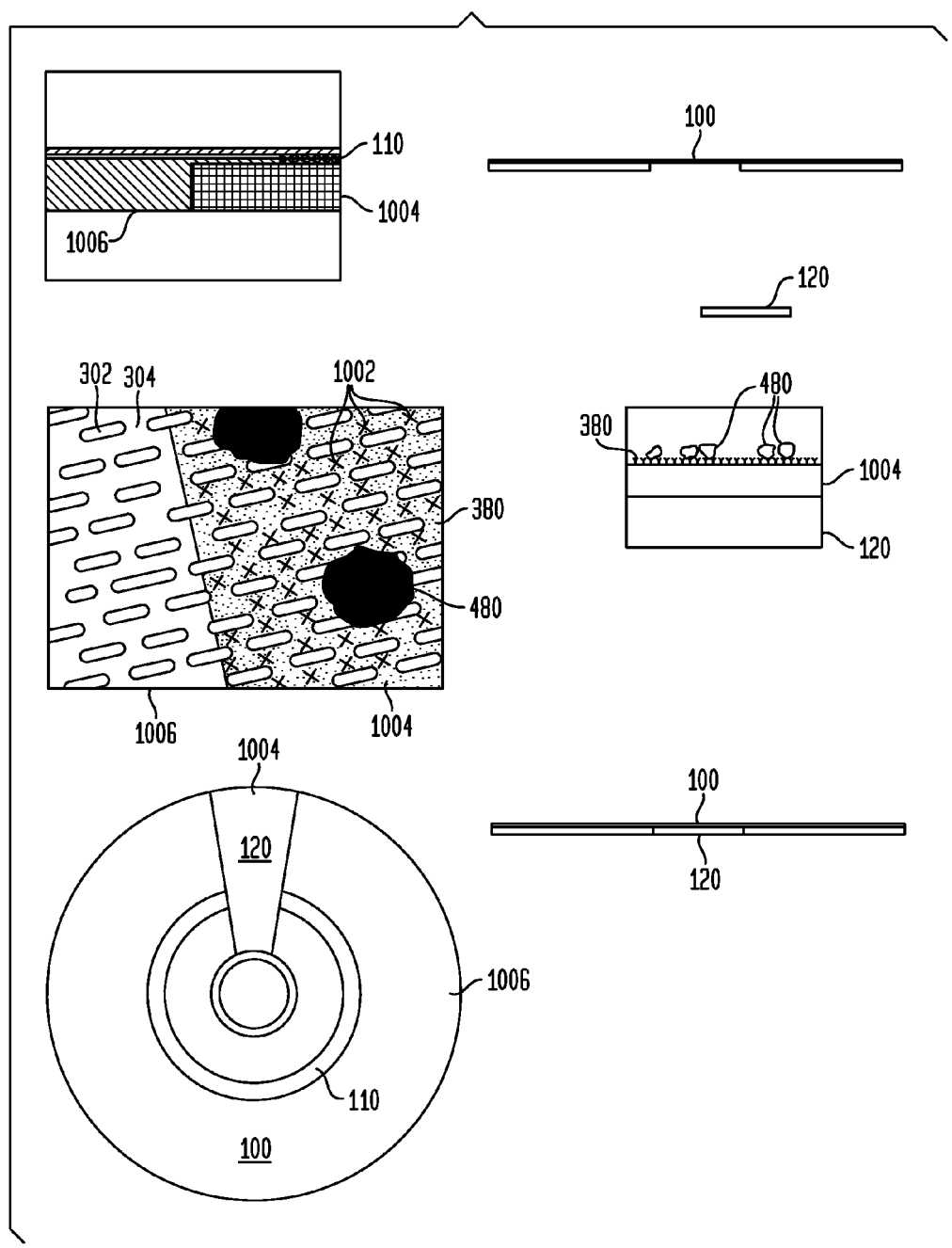
FIG. 10 is a diagram depicting one embodiment of the detection system using micropatterned detector sites and a sectional substrate.
Figure 11:
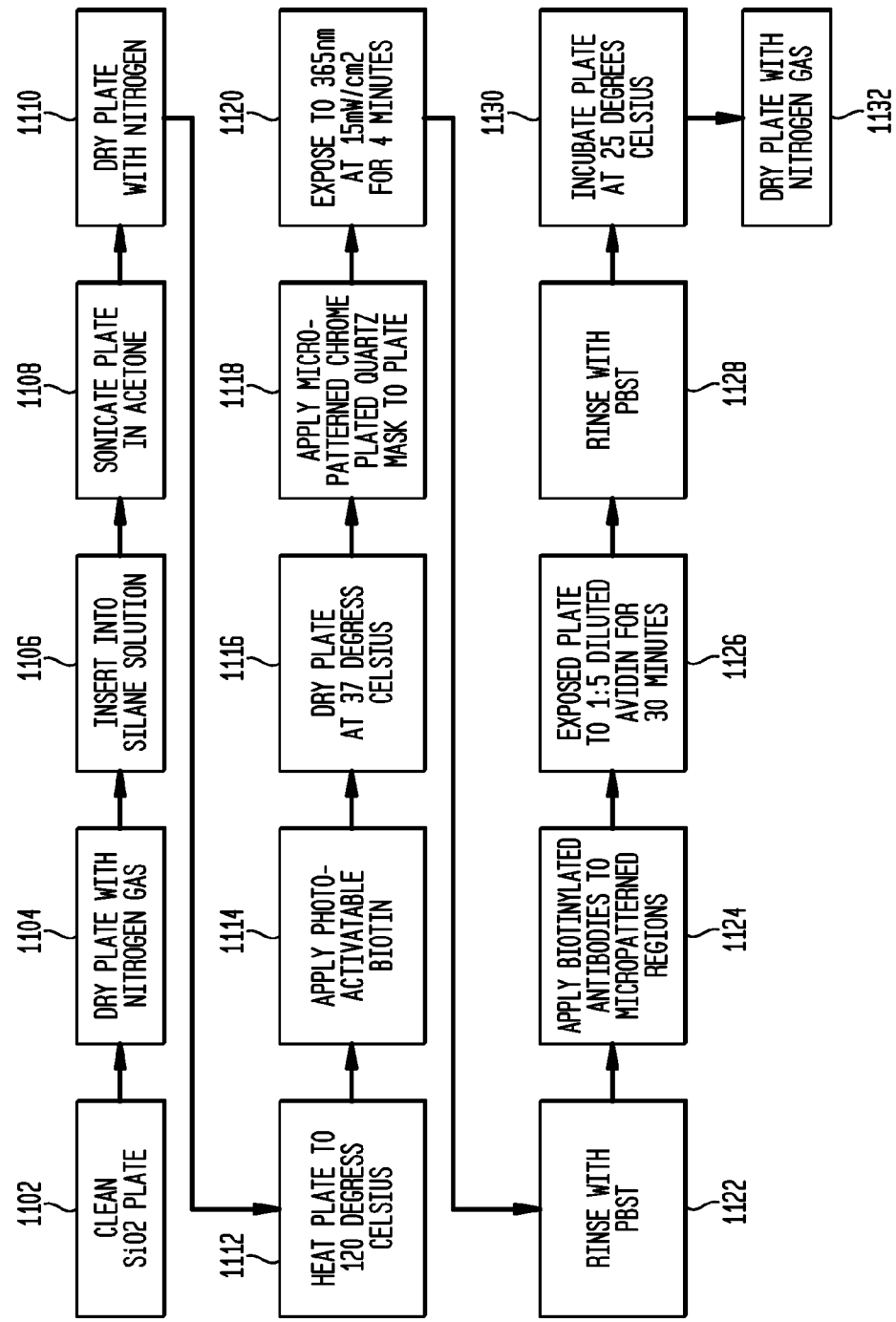
FIG. 11 is a block diagram of one process used to affix a generic detector ligand to a detector substrate using photoactivatable biotins.

FIG. 9 graphically illustrates the process steps associated with the fabrication and integration of a substrate 310 with continuous data spiral 110 comprised of a pregroove 308 and a writeable material 314 with no specific baseline information, referred to as a blank writeable substrate 900, with a detector substrate 350.

The blank writeable substrate 900 is comprised of a substrate 310 with pregroove 308, writeable material 314 and reflective material 340. The blank writeable substrate 900 is encoded with baseline data 902 to create a baseline data substrate 904 using an encoding process. The encoding process 980 uses focused radiation 222 to selectively burn away, ablate, or change the phase of selected portions of the writeable material 314 to adjust the amount of reflected radiation 224 converted by the radiation detector 240, thus storing baseline data 902. The baseline data 902 is selected based on the configuration of detector chambers 130 and fluidic passages 360 selected for the detector substrate 350 as well as the type of detector ligands 380 and the relative absorption of the bound detector ligands 480 to the focused radiation 222 used by the disk system 200.

The baseline data substrate 904 has a series of interlocking features, 920, 922, 924, and 926. The interlocking features in this embodiment include a semi-circle 920, a triangle 922, a trapezoid 924, and a square 926. These interlocking features 920, 922, 924, and 926 are adapted to fit within the corresponding interlocking receptors 910, 912, 914, and 916 on the detector substrate 350, enabling the detector substrate to slide into and become substantially rigidly affixed 988 to the baseline data substrate 904. In other embodiments the interlocking features are reversed with the interlocking receptors 910, 912, 914, and 916 located on the baseline data substrate 904 while the interlocking features 920, 922, 924 and 926 are located on the detector substrate 350.

A blank detector substrate material 952 is used to create the detector substrate 350. The blank detector substrate 952 is comprised of different materials based on the type of detector ligands 380, analyte 960 and focused radiation 222 used to read the biosensor disk 100. The blank detector substrate 952 materials are selected from the materials described above, including but not limited to polycarbonate, polystyrene, and silicon. The blank detector substrate 952 undergoes a fabrication process 982 to create the detector chambers 130, and optionally other fluidic structures including, the fluidic passages 360, and microfluidic control structures such as filtration block 540, removable barrier 530, passive heaters 520, active heaters 522, electrophoretic elements 560, and additional sensors 524 as needed for detecting the one or more analytes 960. In the case of silicon, the fabrication process 982 can comprise multiple steps to create a variety of different fluidic structures and detector chambers 130 desired to process a given sample 950 to determine the analyte(s) 960 contained therein. The silicon fabrication process 982 can utilize standard microelectromechanical systems (MEMS) or microsystems technology (MST) fabrication techniques in addition to microelectronic fabrication techniques as described in greater detail above. For embodiments constructed from plastic, such as polycarbonate or polystyrene, the fabrication process 982 is nominally a thermal assisted molding process, or injection molding process, as described in greater detail above.

The fabrication process 982, in this embodiment, also creates the interlocking receptors 910, 912, 914, and 916 that interlock with the interlocking features 920, 922, 924, and 926 respectively. The interlocking receptors include an interlocking semi-circle 910 receptor, an interlocking triangle 912 receptor, an interlocking trapezoid 914 receptor, and an interlocking square 916 receptor.

After creating the detector substrate 350, the next step in the process for creating an integrated biosensor disk 100 is to affix the detector ligands 380 to the detector chambers 130 on the detector substrate 350. In the case of embodiments where the detector chambers 130 are integrated with the substrate 310, the fabrication process 982 is applied to the substrate 310 to create both the continuous pregroove 308, or alternatively is used to create the pits 302 and land 304 along the continuous data spiral 110 necessary to create the baseline data 902 for interpreting the results during the same fabrication process that creates the detector chambers 130.

Process for Binding Detector Ligands to Detector Chamber

The binding process 984 for binding detector ligands 380 to the detector chamber 130 varies according to the detector substrate material 350, the detector ligands 380 being used and the process steps required to affix the detector ligands 380 to the surface of the detector chambers 130.

Detector Ligand Selection

The detector ligands 380 that are used to bind to the analyte 960 for form bound detector ligands 480 are selected from a wide range of different classes of compound known to those of ordinary skill in the art.

In one embodiment, the detector ligands 380 are selected to detect one or more analytes 960 in a sample 950. Common system for detector ligands 380 are based on avidin/streptavidin-biotin systems. These systems can be used for enzyme immunoassay systems, glycoconjugate analysis, and DNA detection systems. One embodiment of creating the detector ligands 380 utilizes a labeled avidin-biotin system. The labeled avidin-biotin system uses a biotinylated primary antibody bound to the detector chamber 130 to create the detector ligand 380. The primary antibody binds with the antigen by incubating the sample 950 in the detector chamber 130 with the addition of an avidin-enzyme conjugate. The additional avidin enzyme conjugate can be added to the detector chamber 130 through a secondary addition of fluids, or by opening a removable barrier 530 and allowing the avidin-enzyme conjugate to enter the detector chamber 130. The avidin-enzyme conjugate changes the relative transmissivity of the bound detector ligand 480, thereby enabling the disk system 200 to distinguish the presence of the analyte 960 due to the reduced reflected radiation 224 at a specific spot 250 corresponding to the detector chamber 130 with the bound detector ligand 480 using the labeled avidin-biotin system. In an alternative embodiment, the avidin enzyme of the labeled avidin-biotin system responds to the focused radiation 222 by fluorescing or reflecting the reflected radiation 224 to a greater extent or by increasing the transmissivity of the bound detector ligand 480 relative to the unbound detector ligand 380, thereby indicating that there is a bound detector ligand 480 through the increased reflected radiation 224 at a given spot 250. All of the system presented herein provide feedback on the presence of the analyte 960 through either decreased transmissivity, or increased transmissivity or increased reflectance, thereby changing the relative reflected radiation 224 detected by the radiation detector 240.

A second type of avidin/streptavidin-biotin system for use as a detector ligand 380 used a bridged avidin-biotin system. The bridged avidin-biotin system uses avidin as a bridge between a biotinylated secondary antibody and a biotinylated enzyme that is used to change the transmissivity or reflectivity of the bound detector ligand 480 so that bound detector ligand 480 can be picked up by the disk system 200.

In both of these avidin/streptavidin-biotin systems, the detector ligand 380 is bound as part of the binding process 984 to a detector chamber 130 using processes known to one of ordinary skill in the art. In one example, a specific detector chamber 130 or detector chambers 130 for multiple sensitivity are selected for application of the given detector ligand 380. The detector chamber 130 is first prepared to ensure there are residual materials or chemicals remaining from the fabrication process 982. In this embodiment, a temporary protective cover is placed over the other areas of the detector substrate 350 in preparation for application of the detector ligands 380 and to protect detector ligands 380 that have already been integrated with the detector substrate. In other embodiments, robotic dispensers are used to precisely deposit the fluids into the detector chambers 130. For the first step a suitable substrate for immobilizing the detector ligands 380 must be created. In the case of silicon, this can be accomplished by a number of means known to those of ordinary skill in the art including, but not limited to, introducing an activated carboxyl group on the surface of a diamond like carbon coated (DLC) silicon forming the detector chamber 130. Many polymers are activated by oxidating the polymer materials forming the inside of the detector chamber 130 using an organic acid. After the detector chamber 130 is prepped for binding to the detector ligand 380, the detector ligand 380 is introduced into the detector chamber 130. The detector ligand 380 is held at an elevated temperature to promote binding of the detector ligand 380 to the prepared surface of the detector chamber 130. Typically the more concentrated the solution of detector ligands 380, the longer the hold, and the better activated the surface of the detector chamber, all impact the adhesion of the detector ligands 380 to the detector chamber 130. After the detector ligands 380 are affixed to the detector chamber 380, the detector substrate 380 is ready for exposure to the sample 950 that may or may not contain one or more of the analytes 960.

There are many other types of detector ligands 380 that can be integrated with the detector chambers 130 of the biosensor disk 100. The selection of specific types of detector ligands 380, the chemistry of the detector ligands 380, and the binding of the detector ligands 380 to the biosensor disk, and the process for exposing the detector ligands 380 to the sample 950 will vary according to the type of analyte 960 to be detected and the capabilities of the disk system 200, including but not limited to the diameter for the spot 250, the configuration of the disk system 200, e.g. linear, non-prismatic, or prismatic, the sensitive of the radiation detector 240, and the characteristics of the focused radiation 222 used to detect bound detector ligands 480. Some examples of alternative detector ligands include:

- A detector ligand 380 formed from complementary DNA (cDNA) produced from cellular messenger RNA using reverse transcription polymerase chain reaction (RT-PCR) to enable detection of messenger RNA.
- A detector ligand 380 formed using DNA spotting technology using oligonucleotide genome sets;
- Peptide based detector ligands 380 with receptors optimized to bind to specific metals or chlorinated substances.

Exposure of Detector Substrate to Sample

Referring again to FIG. 9, the detector substrate 350 with detector ligands 380 placed inside the detector chambers 130 is ready to be exposed 986 to the sample 950. The sample 950 in this embodiment is contained within a sample chamber 906. The detector substrate 350 is exposed 984 to the sample 950 that may or may not contain the analytes 960 by emersion in the sample chamber 906. The detector substrate 350 is held inside the sample chamber 906 for sufficient time to ensure adequate wetting of the detector chambers 130. After the detector substrate 350 is wetted, it is removed from the sample 950 and any secondary processes necessary to ensure binding of the analyte 960 to the detector ligands 380 is performed. In other embodiments, the sample 950 is taken from the sample container 906 and placed on the detector substrate 350 using the fluidic passages 360 described above, including but not limited to the top surface input passage 506, the bottom surface input passage 508, the input hub chamber 504, and directly into the detector chambers 130.

Integration of the Baseline Data Substrate with the Detector Substrate

The encoding process 980 for the embodiment shown in FIG. 9 is performed prior to integration of the baseline data substrate 904 with the exposed detector substrate 350. During the assembly process 924, the adhesive backing (not shown) on the exposed detector substrate 350 is removed. The exposed detector substrate 350 is aligned with the inside of the baseline data substrate 904 and aligned so the interlocking receptors 910, 912, 914, and 916 on the exposed detector substrate 350 accept the interlocking features 920, 922, 924, and 926 and pushed into the baseline data substrate 904 along the arrows 9A. Once the exposed detector substrate 350 is affixed to the baseline data substrate 904, the biosensor disk 100 is ready for analysis to determine the presence of the analyte 960 in the sample 950. Alternative orders for assembly of the substrate 310 with the detector substrate 350 are integrated into the biosensor disk 100 and exposure of the biosensor disk and/or the detector substrate 350 to the sample 950 are apparent to those of ordinary skill in the art.

Variable Thickness Detector Substrate

In yet another embodiment of the detector substrate 350, the material of the detector substrate 350 is changed in the vicinity of the detector chamber 130. The material change can be either substitution of a material with a different refractive index in the vicinity of the detector chamber 130 or alternatively a lens shaped structure in the vicinity of the detector chamber 130 necessary to ensure the spot 250 of the focused radiation 222 falling on the continuous data spiral 110 remains approximately the same size regardless of whether the spot 250 is traveling over a detector chamber 130 with less material between the top surface 140 and the continuous data spiral 110 or over an area with the nominal amount of material between the top surface 140 and the continuous data spiral 110 to the lack of a detector chamber 130 located therein. Varying the refractive index or thickness of the detector substrate 130 enables relatively constant reflected radiation 224 thereby minimizing the risk of excessive excursion of the focusing lens 221 by the lens position 220 attempting to refocus the focused radiation 222 over a detector chamber 130.

Baseline Information on Continuous Data Track

In the embodiments shown in FIGS. 3, 4 and 5, the background information is stored on the continuous data spiral 110 using the combination of pits 302 and lands 304 of a permanently recorded continuous data track 100 or alternatively with the different phase change or burned off areas of material that provide different reflectivity from the unchanged data encoding material 314. The radiation spot 250 directed to the surface of the continuous data track 110 is reflected back to the disk system 200 different depending on whether or not the radiation spot 250 is directed on a pit 302 or land 304 or a part of the material where it has changed phase or has been burned away. The amount or flux of reflected radiation 224 detected by the radiation detector 240 thus changes as the radiation spot 250 moves over the continuous data spiral 110. Each time the total radiation flux on the radiation detector 240 changes, the output of the radiation detector 240 rises or falls depending on its locating either pit 302 to land 304 transition or a land 304 to pit 302 transition. The change of total radiation flux can thus be used to encode and capture binary information in the surface of the biosensor disk 100. In the embodiment of the disk system 200 shown in FIG. 2, the radiation detector 240 can be used to average of the signals from all four detectors (242, 244, 246, and 248). As the average reading from all four detectors either dips or rises, the change is characterized as either a 0 or 1. In this manner binary information is encoded on the surface of the biosensor disk 100.

Information is recorded in the pits 302 and land 304 or using the continuous pregroove 308 and the writeable material 314 by the amount of time spent as either a zero of a one. The standard used by standard CDs and DVDs to encode data uses eight to fourteen modulation (EFM). The EFM system avoids pits 302 that are too short, too close together, or too long by requiring that there are always at least two 0 bits between any 1 bit, and ensuring there are no more than ten 0 bits between any 1 bit. Therefore the size of any given pits 302 or land 304 is never smaller than 3 T (T defined as the time necessary to encode a single bit of data) and never longer than 11 T. With standard CD velocities and spacing, this means that the smallest pit 302 or land 304 is between about 278 nm to about 324 nm, while the largest pit 302 or land 304 is between about 3054 nm to about 3563 nm.

Error Correction System of Standard CD Type Read/Write Systems

EFM encoding is sequentially applied to a series of bytes called a frame. A frame holds 24 bytes of user data, 1 byte of subcode data, and 8 bytes of parity (error correction), for a total of 33 bytes. Each frame as encoded on the continuous data spiral 110 is preceded by a 24-bit synchronization pattern and 3 merging bits. The sync data has a unique pattern not found elsewhere on continuous data spiral 110, and it ensures the disk system 200 correctly finds the start of the frame. The pattern is in binary form [100000000001000000000010] or three transitions separated by 11 T, which can't occur otherwise because the merging bits are specifically chosen to prevent it. The sync data provides a means for the disk system 200 to locate specific information on the surface of the biosensor disk 100.

The rest of the 33-byte frame is read as 14-bit EFM values followed by 3 merging bits. Therefore a total of 588 (24+3+(14+3)*33) raw binary bits are encoded in the channel frame. The merging bits are removed from the channel frame followed by an EFM decoding process recreates the 8-bit data from the 14-bit data contained within the channel frame to create the F3 Frame. The subcode byte is removed to create the F2 Frame that is passed to a Cross-Interleave Reed-Solomon (CIRC) decoder. The CIRC decoder processes the F2 Frame through two cascaded error correction stages, C1 and C2. Errors within each error correction state are indicated the letter E followed by the type of error (i.e. 1=single symbol correctable errors; 2=-double-symbol correctable errors, and 3 indicates triple-symbol uncorrectable errors) and the CIRC decoder state of the error. For example, an error code of E31 or E32 indicates an uncorrectable error in the C1 and C2 decoder stages respectively. The sum of the E11, E21, and E31 over one second, averaged over 10 seconds of data provides a measure of BLER or block error rate. BLER provides an estimate of the number of errors located at the C1 stage of the CIRC decoder. Since BLER and C1 stages errors are indicative of primarily single bit errors, most bound detector ligands 480, since they are significantly larger than even the maximum size encoded raw physical bit (11 T) may cause significant C1 and BLER errors, however it is harder to distinguish.

The E12 count indicates the number of single-symbol (correctable) errors in the C2 decoder. The sum of E21 and E22 form a burst error count (BST), which can be used to identify the present of bound detector ligands 480 on a biosensor disk 100.

E32 errors, representing triple-symbol (uncorrectable) errors in the C2 decoder, results in damaged data being read from the baseline data track. For an audio disk system 200 an interpolation is performed between the prior non-E32 frame and the next non-E32 frame to minimize the effect of the E32 error. This interpolation requires the amount of displaced data from a bound detector ligands 480 to be relatively large, or the changes in the baseline data 902 to be large in order to maximize the potential for a given interpolation to be heard 824. The likelihood of the bound detector ligands 480 to generate an audible signal in the presence of the error correction is increased by locating multiple detector chambers 130 across a number of successful physical data tracks 112.

In embodiments with computer processing the resulting data direct inspection of the digital errors are possible and it is possible to correlate the relative errors rates for a specific frame of data to the relative expression of detector ligands 380 in a given detector chamber 130.

In either embodiment of the biosensor disk 100, regardless of whether information is encoded using a writeable material 314 or using a series of pits 302 and land 304 located in the substrate 310, the biosensor disk 100 is encoded with baseline data 902. The baseline data 902 is selected to provide a discriminating signal using knowledge of the disk system 200, including the methodology for encoding raw binary information in the baseline data 902 and the decoding and error correction schemes applied to the baseline data 902 as it is received from the biosensor disk 100 while it is read by the disk system 200. The discriminating signal encoded in the baseline data 902 provides a background information suitable for distinguishing the impact of the bound detector ligands 480 on the reflected radiation 224, thereby providing feedback to the user regarding the relative expression or number of bound detector ligands 480 present in the system.

The baseline data 902, in some embodiments also contains information encoded about the type of sensor being queried on a given logical track. The logical track is a superset of physical tracks 112 and a subset of the continuous data spiral 110 that comprise information related to the same information. In addition to providing information about the type of detector chambers 130 and detector ligands 380 located along a specific logical track on the continuous data spiral 110, the baseline data 902 provides a background digital signal from the reflected radiation 224 that the bound detector ligands 480 interrupt in a known way. The interruption caused by the bound detector ligands 480 interacts with the disk system 200, including the error correction and encoding systems, to create a signal that is processed and presented to the user or processed and output 818 as aural signal for generation 820 by a speaker into audio waves that travel 822 through the air so the changes caused by the bound detector ligands 830 to the baseline data 902 are heard 824.

Sectional Substrate Method for Detection Through Digital Substrate Interference and Interrogation Method In still other embodiments, the analyte detector region 120 has detector ligands 380 micropatterned 1002 onto the surface of the analyte detector region 120. The detector ligands 380 are preferably micropatterned 1002 to be approximately at or just below the detection threshold of the system, such that when an analyte 960 is present the path for returned light from the continuous data spiral 110 is interrupted sufficiently to produce at least one detectable error, for example a C1, C2 or CU error, when the continuous data spiral 110 is read by the system.

In one embodiment, the micropatterning 1002 is accomplished by utilizing a photochemical process, for example using a chrome plated quartz mask as is known in the art. An SiO2 substrate with a grown oxide layer, such as one commercially available from 3M, is cleaned and sterilized 1102 using, for example, pyrogenic steam. Then the surface is nitrogen dried 1104 and inserted into a 2% Silane, Si(CH2)3, solution 1106, incubated and then sonicated in acetone 1108 before being nitrogen dried again 1110. Heating to 120 degrees Celcius 1112 produces a dense smooth substrate of Silane, Si(CH2)3, on SiO2. Applying photoactivatable biotin 1114, for example using the one commercially available from Pierce, in a 2:9 solution with deionized water, one then presses it with a glass slip and bakes dry at 37 degrees Celcius 1116. Finally, the micropatterned chrome plated quartz mask is placed 1118 over the photoactivatable biotin and exposed 1120 to 365 nm light at 15 mW/cm2 for four minutes, before rinsing 1122 with a phosphate buffered saline tween-20 (PBST) multiple times to remove any unactivated biotin. The surface is then exposed 1124 to 1:5 diluted Avidin for 30 minutes and rinsed again with PBST 1126. Commercially available biotinylated antibodies are then put onto the micropatterned regions 1128, for example using a micropipet, and incubated 1130 at 25 degrees Celcius before being dried with a stream of nitrogen gas 1132.

In other embodiments, micropatterning 1002 is accomplished by microcontact printing, or spotting or spraying of ligands onto the analyte detector region 120. In some embodiments, the micropatterning 1002 is performed on a polycarbonate analyte detector region 120. In other embodiments the analyte detector region 120 utilizes SiO2 for a more durable surface for performing the micropatterning 1002. For example, in some embodiments, a nanometer layer of photobiotin can be applied to untreated SiO2 by applying the photobiotin and then drying the SiO2 at approximately 370 C. SiO2 allows analyte detector regions 120 as thin as 0.25 mm or thinner to be successfully utilized. Because SiO2 has an index of refraction of 1.45 which is different than polycarbonate, in some embodiments the SiO2 is treated with nitrogen until the SiO2 contains approximately 3% nitrogen at which point it will have an index of refraction (IR) approximately equal to the IR 1.55 of polycarbonate. The index of refraction is more important for reflection type CD/DVD systems than for a modified system that uses a transmission approach.

In some embodiments, such as when using a microfluidic channel 360, the SiO2 is treated so that it becomes more receptive to the application of photobiotin and hydrophobic films. Use of hydrophobic films prevents the sample 950 from adhering to any part of the analyte detector region 120 except the detector ligands 380, ensuring that any the blockage of returned light is the result of analytes 960 in bound detector ligands 480 and not due to any extraneous fluid sample 950 that is still present in the analyte detector region 120, or an unbound substance of no interest from the fluid sample 950. To prepare the SiO2, pyrogenic steam is first applied to the surface to clean and sterilize, then the surface is nitrogen dried and exposed to Silane, Si(CH2)3, at approximately 1050 C, and thereafter cooled, creating an approximately 260 nm layer receptive to the application of photobiotin or another hydrophobic thin film. In another embodiment, Silicon Nitride, Si3N4, is applied to the SiO2 by plasma chemical vapor deposition. Silicon Nitride, Si3N4, and Silane, Si(CH2)3, have RIs of approximately 1.46, and it is possible to have an even lower RI in some configurations, for example an RI of 1.33 when a fluid sample is present in a 10 micrometer channel. Therefore, in some embodiments, polyvinyl alcohol or glycol alcohol are included in the sample 950 or added prior to analyzing in order to increase the RI closer to the RI 1.55 of polycarbonate.

In one embodiment the analyte detector region 120 includes detector ligands 380 in a gel or gel-like detection substrate 1004. In another embodiment, the detector ligands 380 are in the form of a thick or thin film detection substrate 1004. The detection substrate 1004 is then docked with the rest of the disk 100 in a socket abutting the data substrate 1006 of polycarbonate that supports the continuous data spiral 110.

In one embodiment, the system uses an unmodified CD/DVD player of a computing device. Most computer CD/DVD players allow applications access to the C1 (Bit Error), C2 (Block Error), and CU (Unrecoverable Error) errors of the CIRC decoding engine which decodes the raw data retrieved from the disk and converts it into usable binary data for applications. Generally, however, applications do not have low level access to the raw data itself, only the usable binary data and the errors. When pits 302 and lands 304 in the continuous data spiral 110 are blocked, for example by one or more bound detector ligands 480, a C1 error is generated. If multiple pits 302 and lands 304 are blocked, a more serious C2 error is generated. Generally, the system can recover the underlying data on the disk for C1 and C2 errors. However, if too much of the data is blocked, the system will generate a CU unrecoverable error.

The detector region 120 is micropatterned 1002 with detector ligands 380, and exposure of the detector ligands 380 to analytes 960 creates bound detector ligands 480 which block pits 302 and lands 304 in the continuous data spiral 110 causing errors to be generated. In one embodiment, the detector ligands 380 are small enough that they, by themselves, do not generate C1, C2 or CU errors. In another embodiment, the detector ligands 380 generate a small baseline number of C1 errors. In both embodiments, when the detector ligands 380 attach to analytes 960 to become bound detector ligands 480, the bound detector ligands 480 generate a greater number of C1 errors that the detector ligands 380 generate alone. This relative difference, or delta, in the number of errors is utilized by the system as an indication that the analyte 960 of interest is present in the sample 950. The bound detector ligands 480 may also generate a number of C2 errors. In one embodiment, the number of C1 and C2 errors can be utilized to indicate relative concentrations of analytes 960 in the sample 950.

In one embodiment, the continuous data spiral 110 is written with data in a pattern that tends to create a random distribution of lands 304 and pits 302, thus preventing clustering of lands 304 or pits 302 in adjacent tracks and any associated detection artifacts that would arise due to the clustering. In an alternate embodiment, the data is written so as to maximize the number of land-to-pit and pit-to-land transitions, thus maximizing the possibility that blockage by a bound detector ligand 480 will create a detectable error.

The shape of the micropatterning 1002 is also partially determinative of the sensitivity of the system to bound detector ligands 480. In one embodiment, the micropatterning 1002 is linear in shape having approximately radial, tangential or other orientations, or combinations thereof. In another embodiment, the micropatterning 1002 is curvilinear, for example by tracking the continuous data spiral 110. Micropatterning 1002 using approximately curvilinear patterns allows detection of bound detector ligands 480 as small as 10 um by 6 um, whereas radial linear patterns allows detection of 15 um×8 um bound detector ligands 480 and tangential linear patterns allows detection of 13 um×7 um bound detector ligands 480. In one embodiment, the system can detect individual bound detector ligands 480. This is typical when the analyte 960 and associated bound detector ligand 480 is large in comparison to individual pits 302 and lands 304. In another embodiment the detector ligands 380 are clustered together such that clusters of bound detector ligands 480 are utilized to trigger at least one C1 error. This is useful for detecting smaller analytes 960 wherein a single associated bound detector ligands 480 may not be large enough to trigger a C1 error reliably by itself.

Additionally, clusters of detector ligands 380 can be specifically micropatterned to block pits 302 and lands 304 and cause errors in a specific detectable pattern and can therefore serve as markers for the system to determine which close by detector ligands 380 are detecting which analytes. For example, a cluster specifically micropatterned 1002 to generate a specific number of C1 errors in a row would identify one analyte 960 detection site, whereas a cluster micropatterned 1002 to generate a pattern of high-low-high-low C1 errors in a row would identify a different analyte 960 detection site. These clusters would permit alignment of analyte 960 detection sites without having to also line up data markers in the underlying continuous data spiral 110.

In one embodiment the detector region 120 is roughly rectangular with parallel sides and is placed in a corresponding socket in the biosensor disk 100. In another embodiment, the detector region 120 is roughly pie-slice shaped and has sides that diverge the further they are displaced from the center 101, for example the sides can be portions of a radius of the biosensor disk 100. In another embodiment, the detector region 120 is circular in shape and is placed over the underlying disk to form the biosensor disk 100. In some embodiments, the detector region 120 forms an internal chamber between it and the rest of the biosensor disk 100 and may include a fluid channel 360, whereas in other embodiments the detector region 120 is an exposed surface application.

In alternate embodiments, the error correction and CIRC circuitry is bypassed, allowing direct access to the raw data stored on the continuous data spiral 110. The raw data would be compared with a reference data to determine which pits 302 and lands 304 were being blocked and therefore which detector ligands 380 had associated analytes 960 attached to them. In another embodiment, the data on the underlying continuous data spiral could be specifically encoded or burned to the disk with errors such that blocking of certain pits 302 and lands 304 would force erroneous error correction by the error correction and CIRC circuitry. In this embodiment, the resulting data from the CIRC would be compared with a reference data to infer which pits 302 and lands 304 were being blocked and causing the erroneous CIRC correction and therefore which detector ligands 380 had associated analytes 960 attached to them. These alternate embodiments have the advantage that the system could detect the detector ligands 380 even when they are in the code and subcode sections of the continuous data spiral 110, but may result in the system not being compatible with all hardware manufacturers and CD/DVD players.

Conclusion

The embodiments of the invention shown in the drawing and described above are exemplary of numerous embodiments that may be made within the scope of the appended claims. It is contemplated that numerous other configurations of an electromagnetic biosensor system, device, and method and process for detecting analytes may be created taking advantage of the disclosed approach. It is the applicant's intention that the scope of the patent issuing herefrom will be limited only by the scope of the appended claims.

What is claimed is:

1. A system for detecting one or more analytes in a sample using a biosensor, comprising:
   a biosensor disk, with an outer surface and a layer encoded with a data path capable of being read by an electromagnetic radiation incident upon said layer, said data path encoded with a baseline data that is static;
   a detector chamber disposed along said data path, said detector chamber having a surface for affixing detector ligands, said surface distinct from said layer encoded with said data path;
   a detector ligand adapted to bind with an analyte, said detector ligand affixed to said surface for affixing detector ligands of said detector chamber, wherein said detector ligand when bound to an analyte creates a detectable change to said electromagnetic radiation; and
   a disk system adapted to accept and rotate said biosensor disk, comprising a source of said electromagnetic radiation focused on said layer encoded with said data path of said biosensor disk, and a sensor adapted to detect said electromagnetic radiation returned from said layer encoded with said data path of said biosensor disk and convert said electromagnetic radiation into an electrical signal.

2. The system of claim 1, wherein said detectable change is selected from the group consisting of: a change in reflection of said electromagnetic radiation, a change in transmission of said electromagnetic radiation, a change in absorption of said electromagnetic radiation, a change in refraction of said electromagnetic radiation, a change in polarization of said electromagnetic radiation, a change in dispersion of said electromagnetic radiation, and a change in diffraction of said electromagnetic radiation.

3. The system of claim 1, wherein said detector chamber is between about 300 nm to about 3000 nm along said data path, wherein said data path is further comprised of a plurality of physical tracks, and wherein said detector chamber is disposed along said data path to interrupt more than one of said physical tracks.

4. The system of claim 1, wherein said data path is encoded with a baseline data to provide a continuous discriminating signal, and said detector chamber is disposed on said data path such that said detector ligand when bound to said analyte changes said electromagnetic radiation returned from said biosensor disk such that a detectable signal change occurs in said electronic signal compared to said electronic signal produced by said baseline data.

5. The system of claim 4, wherein said detectable signal change to said electronic signal appears as a change in said baseline data.

6. The system of claim 1, further comprising:
a threshold circuit to quantize said electrical signal into a binary representation of said electrical signal; and
a digital circuit to construct a digital word from said binary representation and further comprising a CIRC encoder, a first error correction stage, and a second error correction stage that construct a decoded frame from multiple said digital words and outputs errors from said first error correction stage and said second error correction stage.

7. The system of claim 6, wherein said detector chamber is disposed on said data path such that said detector ligand when bound to said analyte changes said electromagnetic radiation returned from said biosensor disk such that a detectable signal change occurs in said electronic signal compared to said electronic signal produced by said baseline data, and said detectable signal change is selected from the group consisting of: an increase in said output errors from said first correction stage, an increase in said output errors from said second correction stage, an increase in said output errors from said first correction stage and said second correction stage, a change in said information of said decoded frame, and an unrecoverable error that results in said decoded frame being improperly reconstructed.

8. The system of claim 1, wherein said detector chambers are oriented on said biosensor disk relative to said data path such that when said electrical signal is transformed into an audio signal, said audio signal varies relative to the number of said detector ligands in said detector chamber that are bound to the analyte.

9. The system of claim 1, wherein said detector chamber is disposed on said outer surface of said biosensor disk and said detector chamber is orientated between said source of electromagnetic radiation and said data path.

10. The system of claim 1, wherein said detector chambers are disposed on a separate detector substrate and further comprising an interlocking feature on said biosensor disk adapted to accept a corresponding mating feature on said separate detector substrate and align said separate detector substrate with said data path.

11. The system of claim 1, further comprising a fluidic passage embedded within said biosensor disk wherein said fluidic passage is in fluidic association with said detection chamber.

12. The system of claim 11 wherein said fluidic passage is selected from the group consisting of an input hub chamber, a top surface input passage, a bottom surface input passage, an interchamber fluidic passage, and an edge exhaust passage.

13. The system of claim 11, wherein said fluidic passage is contained within said biosensor disk and fluidly associates said detector chamber with said outer surface.

14. The system of claim 11, further comprising an input hub chamber adapted to accept the sample, said fluidic passage fluidly connecting said input hub chamber to said detector chamber.

15. The system of claim 1, wherein said biosensor disk further comprises at least one fluidic control device selected from the group consisting of: a filtration block, a removable barrier, a passive heater, an electrophoretic element, an active heater, an input hub chamber, a top surface input passage, a bottom surface input passage, an interchamber fluidic passage, and an edge exhaust passage.

16. The system of claim 1, whereby said rotating of said biosensor disk by said disk system urges the sample to flow in a fluidic passage embedded within said biosensor disk.

17. The system of claim 16, wherein said biosensor disk further comprises:
an inner hub disposed at the center of said biosensor disk; and
an input hub chamber fluidly connected to said detector chambers and adapted to accept the sample.

18. The system of claim 1, whereby said biosensor disk with said detector ligands is exposed to the sample and processed so as to encourage binding of the analyte to said detector ligands.

19. The system of claim 1, wherein said biosensor disk further comprises:
a first logical data track, a second logical data track, and a third logical data track on said data path;
a first detector chamber disposed on said first logical data track, a second detector chamber is disposed on said second logical data track, and a third detector chamber disposed on said third logical data track;
a first detector ligand affixed to said first detector chamber, said first detector ligand adapted to bind with a first analyte and a second analyte, wherein said first detector ligand when bound to the first analyte and the second analyte creates a first detectable change to said electromagnetic radiation;
a second detector ligand affixed to said second detector chamber, said second detector ligand adapted to bind with the second analyte and a third analyte, wherein said second detector ligand when bound to the second analyte and the third analyte creates a second detectable change to said electromagnetic radiation;
a third detector ligand affixed to said third detector chamber, said third detector ligand adapted to bind with the first analyte and the third analyte, wherein said third detector ligand when bound to the first analyte and the third analyte creates a third detectable change to said electromagnetic radiation; and
a means for discriminating between said first detectable change, said second detectable change, and said third detectable change to identify the presence of the first analyte, the second analyte, and the third analyte.

20. The system of claim 1, wherein said detector ligand binds the analyte, and wherein said detector ligand is selected from the group consisting of: an atividin-biotin receptor, a peptide, an olglionucleotide, cDNA, and a chelating agent.

21. The system of claim 1, wherein said detector chamber is adapted to be placed within said biosensor disk and wherein said detector chamber is fabricated from a material selected from the group consisting of: a polymer, and a silicon substrate.

22. A method for detecting an analyte in a sample, comprising:
(a) introducing the sample to a biosensor disk, wherein said biosensor disk is comprised of a layer having a data path encoded with a baseline data that is static and a detector chamber disposed along said data path, said detector chamber having a surface for affixing detector ligands that is distinct from said layer encoded with said data path, said detector chamber further comprising a detector ligand adapted to bind with the analyte, said detector ligand affixed to said surface for affixing detector ligands of said detector chamber;
(b) urging the sample into said detector chamber;
(c) binding the analyte to said detector ligand disposed in said detector chamber to create a bound detector ligand, whereby said bound detector ligand in said detector chamber creates a detectable change to an electromagnetic radiation incident upon said bound detector ligand;
(d) placing said biosensor disk in a disk system;
(e) rotating said biosensor disk with said disk system;

(f) emitting said electromagnetic radiation from said disk system focused on said layer encoded with said data path on said biosensor disk;

(g) receiving a returned electromagnetic radiation from said layer encoded with said data path of said biosensor disk; and (h) interpreting a change in said returned electromagnetic radiation caused by said detectable change to indicate the presence of said bound detector ligand.

23. The method of claim 22, wherein said biosensor disk further comprises a fluid control structure selected from the group consisting of a filtration block, a removable barrier, a passive heater, an electrophoretic element, an active heater, an input hub chamber, a top surface input passage, a bottom surface input passage, an interchamber fluidic passage, and an edge exhaust passage, and wherein said fluid control structure is embedded within the structure of the biosensor disk and wherein said fluidic control structure is utilized in said (b) urging the sample.

24. The method of claim 22, wherein said (b) urging the sample is accomplished by the rotation of the biosensor disk.

25. The method of claim 22, wherein said (h) interpreting a change further comprises a means of outputting said detectable change as an audible signal.

* * * * *